United States Patent [19]
Dren et al.

[11] 4,025,630
[45] May 24, 1977

[54] ANESTHESIA METHODS USING BENZOPYRANS AND ESTERS THEREOF AS PRE-ANESTHESIA MEDICATION

[75] Inventors: Anthony Thomas Dren, Waukegan; Donn Myron Ebert, Lake Zurich, both of Ill.

[73] Assignee: Abbott Laboratories, North Chicago, Ill.

[22] Filed: Sept. 11, 1974

[21] Appl. No.: 505,125

Related U.S. Application Data
[62] Division of Ser. No. 398,616, Sept. 19, 1973.

[52] U.S. Cl. .................................. 424/256; 424/267
[51] Int. Cl.$^2$ ........................................ A61K 31/435
[58] Field of Search ............................ 424/256, 267

[56] References Cited
UNITED STATES PATENTS 3,429,889  2/1969  Shulgin ............................ 260/295

OTHER PUBLICATIONS

Chatteujee, D. K., Indian J. Appl. Chem. (1969), 32(i), pp. 65–68.

Primary Examiner—Jerome D. Goldberg
Attorney, Agent, or Firm—Vincent A. Mallare; Robert L. Niblack

[57] ABSTRACT

Improved anesthesia methods comprising pretreating a patient to be anesthetized with a benzopyran of formula I

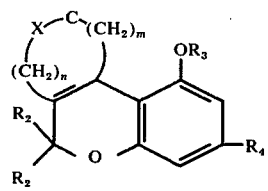

wherein, in the C ring, X is $NR_1$, S, $CH_2$ or

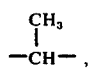

$R_1$ is hydrogen, loweralkyl, loweralkenyl, loweralkynyl, loweralkanoyl, cycloalkyloweralkyl, cycloalkylloweralkanoyl, cycloalkyl, haloloweralkyl, haloloweralkenyl, phenylloweralkyl, phenyloweralkenyl or phenyloweralkylnyl; $m$ is an integer from 0 to 3, $n$ is an integer from 0 to 3 and $n + m = 2$ or 3; or the C ring is quinuclidine ring

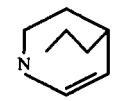

$R_2$ is loweralkyl; $R_3$ is hydrogen or

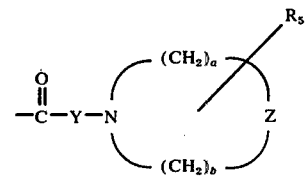

wherein Y is a straight or branched chain alkylene group having from one to eight carbon atoms, $a$ is an integer from 1 to 4, $b$ is an integer from 1 to 4, Z is $CH_2$, O, S or $NR_6$, $R_6$ being hydrogen or loweralkyl, with the limitation that when Z is O, S or $NR_5$, the sum of $a$ and $b$ is 3 or 4, and $R_5$ is hydrogen or loweralkyl; $R_4$ is $C_1$–$C_{20}$ straight or branched chain alkyl, cycloalkyl, or

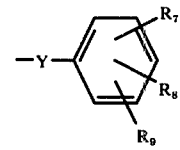

wherein Y is a straight or branched chain alkylene group having from one to ten carbon atoms, and each $R_7$, $R_8$ and $R_9$ are the same or different members of the group consisting of hydrogen, halo, trifluoromethyl or loweralkyl; and the pharmaceutically acceptable salts thereof, with the limitation that when X is

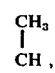

$m = 2$ and $n = 2$, $R_3$ cannot be hydrogen.

7 Claims, No Drawings

ANESTHESIA METHODS USING BENZOPYRANS AND ESTERS THEREOF AS PRE-ANESTHESIA MEDICATION

This is a division of application Ser. No. 398,616, filed Sept. 19, 1973.

BACKGROUND OF THE INVENTION

General anesthetics, a select group of central nervous system depressants, which have the capacity to produce a rapidly reversible loss of consciousness, analgesia and muscle relaxation, are used principally to reduce patient awareness or recall of distressing or painful surgical procedures. Representatives of thi group include (1) barbituate derivatives such as Pentothal (sodium thiopental) for intravenous use, (2) volatile liquid inhalation anesthetics suchas Fluorthane (halothane) and Penthrane (methoxyflurane) and (3) gases such as cyclopropane and nitrous oxide.

Anesthesia produced by either the intravenous or inhalation agents creates a certain degree of risk to the patient. The pharmacologic, physical-chemical and pharmacokinetic properties of these agents require that extreme caution be used when they are utilized for surgical anesthesia. When amounts slightly larger than the anesthetic dose are given, these agents can be lethal. Because of their high lipid solubility, the use of general anesthetics in obese patients can pose a particular problem because larger amounts of drug are required to induce anesthesia. These agents, being retained in fatty tissues, will take longer to dissipate in these individuals. The metabolic conversion products of some anesthetics, especially the volatile liquids, can produce dose related toxicities including liver and kidney damage.

The search for improved general anesthetics continues, as well as the search for means of producing the same therapeutic effect using lesser amounts of the known anesthetic agents. The present invention provides a means of inducing the same degree of anesthesia with less of the anesthetic agent by pre-treating a patient to be anesthetized with a benzopyranopyridine. The benzopyranopyridines have no anesthetic activity themselves. However, when patients are pre-treated with the benzopyrans useful in the practice of this invention, the onset of anesthesia is shortened and duration of anesthesia is significantly lengthened, without increasing the mortality rate. In other words, the same degree of anesthesia can be produced with far less anesthetic agent when a patient is pre-treated with the compounds useful in the practice of this invention.

While it is common to pretreat patients prior to anesthesia, the agents used are not necessarily anesthetics in and of themselves and have no demonstrated synergistic effect on a particular anesthetic. Rather, the pre-anesthetic medications often serve to relax the patient prior to surgery as well as diminish the undesirable side effects common to many general anesthetics.

DETAILED DESCRIPTION OF THE EMBODIMENTS OF THE INVENTION

This invention relates to improved methods of producing anesthesia with either fixed or inhalation anesthetics by pre-treating patients with a benzopyran of formula I

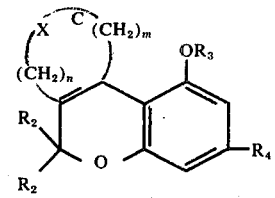

wherein, in the C ring, X is $NR_1$, S, $CH_2$ or

$R_1$ is hydrogen, loweralkyl, loweralkenyl, loweralkynyl, loweralkanoyl, cycloalkylloweralkyl, cycloalkylloweralkanoyl, cycloalkyl, haloloweralkyl, haloloweralkenyl, phenylloweralkyl, phenylloweralkenyl or phenylloweralkynyl; $m$ is an integer from 0 to 3, $n$ is an integer from 0 to 3 and $n + m = 2$ or 3; or the C ring is a quinuclidine ring

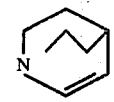

$R_2$ is loweralkyl; $R_3$ is hydrogen or

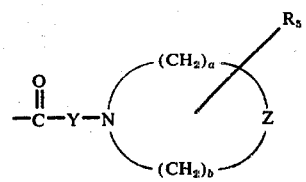

wherein Y is a straight or branched chain alkylene group having from one to eight carbon atoms, $a$ is an integer from 1 to 4, $b$ is an integer from 1 to 4, Z is $CH_2$, O, S, or $NR_6$, $R_6$ being hydrogen or loweralkyl, with the limitation that when Z is O, S or $NR_5$, the sum of $a$ and $b$ is 3 or 4, and $R_5$ is hydrogen or loweralkyl; $R_4$ is $C_1$–$C_{20}$ straight or branched chain alkyl, cycloalkyl, or

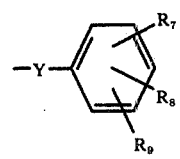

wherein Y is a straight or branched chain alkylene group having from one to ten carbon atoms, and each $R_7$, $R_8$ and $R_9$ are the same or different members of the group consisting of hydrogen, halo, trifluoromethyl or loweralkyl; and the pharmaceutically acceptable salts thereof, with the limitation that when X is

$m = 2$ and $n = 2$, $R_3$ cannot be hydrogen.

As used herein, the term "loweralkyl" refers to $C_1$–$C_6$ straight or branched chain alkyl groups including methyl, ethyl, n-pentyl, iso-pentyl, neo-pentyl, n-propyl, iso-propyl, n-butyl, sec-butyl, tert-butyl, n-hexyl and the like.

The term "loweralkenyl" refers to straight and branched chain $C_2$–$C_6$ alkyl radicals from which a hydrogen atom has been removed from each of two adjacent carbon atoms to produce ethylenic unsaturation; e.g., vinyl, allyl, methallyl, 1-pentenyl and the like.

The term "loweralkynyl" refers to $C_2$–$C_6$ alkyl groups as defined above, from which two hydrogen atoms have been removed from each of two adjacent carbon atoms to produce acetylenic unsaturation; e.g., ethynyl, propargyl, 2-butynyl, 1-pentynyl and the like groups.

The term "halo" includes chloro, fluoro, bromo and iodo.

The term "loweralkanoyl" refers to saturated monovalent, aliphatic radicals derived from a monocarboxylic acid, including straight or branched chain radicals of from one to six carbon atoms including the formyl, acetyl, propionyl, β-methylpropionyl, butyryl, hexanoyl and the like radicals.

"Cycloalkyl", as used herein, refers to cyclic saturated aliphatic radicals having three to eight carbon atoms in a ring, such as cyclopropyl, cyclobutyl, cyclopentyl, cyclohexyl, cycloheptyl and cyclooctyl.

"Cycloalkylloweralkyl" refers to groups such as cyclopropyl-methyl, 2-methylcyclobutyl and the like.

The term "alkyl" refers to straight and branched chain alkyl radicals having from one to twenty carbon atoms such as methyl, n-amyl, 3-methyl-2-octyl, 2-nonyl, 2-eicosanyl and the like.

The term "pharmaceutically acceptable acid addition salts" refers to non-toxic salts prepared by reacting the basic esters of the benzopyranopyridines with an organic or inorganic acid, or by reacting the benzopyranopyridines with the salt of an appropriate acid. Representative salts include the hydrochloride, hydrobromide, sulfate, bisulfate, acetate, valerate, oleate, laurate, borate, benzoate, lactate, phosphate, tosylate, citrate, maleate, succinate, tartrate, napsylate and the like.

When $R_3$ is hydrogen, the term "pharmaceutically acceptable salts" refers to the alkali earth, alkali metal, ammonia and substituted ammonium salts such as the sodium, potassium, aluminum, magnesium, benzylammonium, methylammonium, dimethylammonium and like salts.

The following formulae illustrates the compounds useful in the practice of this invention.

When X is $NR_5$ and $n$ is 2 and $m$ is 1, the compounds useful in the practice of this invention are represented by formula II

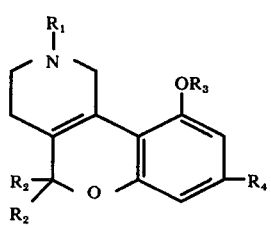

When X is $NR_5$, $m$ is 1 and $n$ is 1, the compounds are represented by formula III

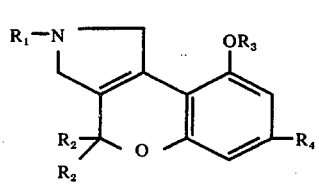

When X is S and $m$ and $n$ each are one, the compounds are represented by formula IV

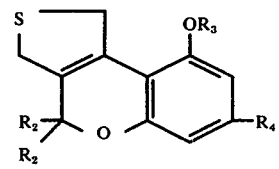

When X is S, $m$ is 2 and $n$ is zero, the compounds are represented by formula V

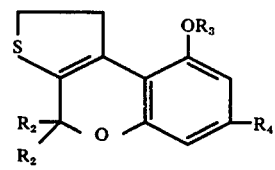

When X is S, $n$ is 2 and $m$ is zero, the compounds are represented by general formula VI

VI

When X is S, $n$ is 2 and $m$ is one, the compounds are represented by formula VII

VII

When X is S, $n$ is 3 and $m$ is zero, the compounds are represented by formula VIII

VIII

When X is $CH_2$ and the sum of $m + n = 3$, the compounds are represented by formula IX

IX

When X is

m is 2 and n is 1, the compounds are represented by formula X

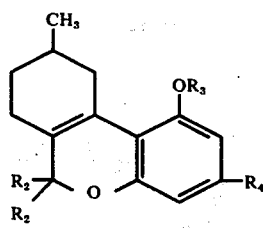

X

When X is $NR_1$, m is two and n is one, the compounds are represented by formula XI

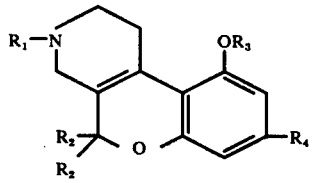

XI

When the C ring is a quinuclidine ring, the compounds are represented by formula XII

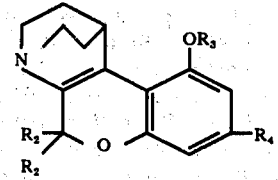

XII

When $R_3$ is hydrogen and R is alkyl or cyloalkyl, the compounds are prepared according to U.S. Pat. No. 3,576,798. The corresponding esters, $R_3$ equals

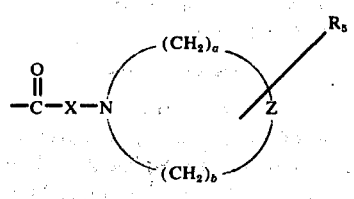

are prepared by equimolar amounts of the phenolic benzopyranopyridines with an appropriate acid or salt thereof in the presence of a carbodiimide such as dicyclohexyl carbodiimide and a suitable solvent such as methylene chloride, chloroform and the like. This reaction can be represented as follows:

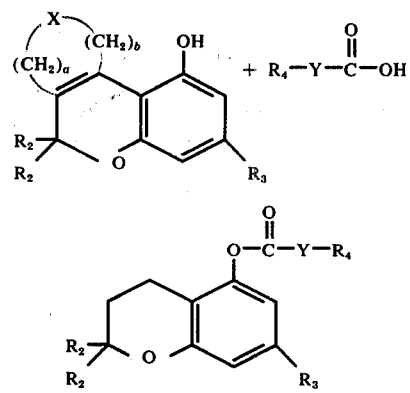

Some of the heterocyclic acids which can be used in the process of preparing the esters of this invention are:
γ-piperidinobutyric acid,
γ-morpholinobutyric acid,
γ-(2-methylpiperidino)-butyric acid,
δ-piperidinovaleric acid,
γ-pyrrolidinobutyric acid,
β-piperidinopropionic acid,
γ-thiomorpholinobutyric acid and homopiperidinoacetic acid Reaction between the benzopyrane starting material and the heterocyclic acid, or salt thereof, is readily effected by combining about equimolar amounts of the reactants and a slight excess of carbodiimide such as dicyclohexylcarbodiimide. The reaction proceeds readily at room temperature and is generally completed in about 4 to 20 hours. After the reaction is terminated, the reaction mixture can be filtered to remove the by-product of dicyclohexylurea, and the solvent can be distilled off using a rotary evaporator. The residue can be directly crystallized from a suitable solvent such as benzene/ether or the residue can be chromatographed and the desired material isolated from the appropriate chromatographic fractions. If the basic esters are obtained, the acid addition salts such as those named above, if desired, can be prepared by methods well known in the art.

Compounds wherein $R_4$ is

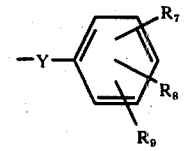

can be prepared according to the following reaction scheme:

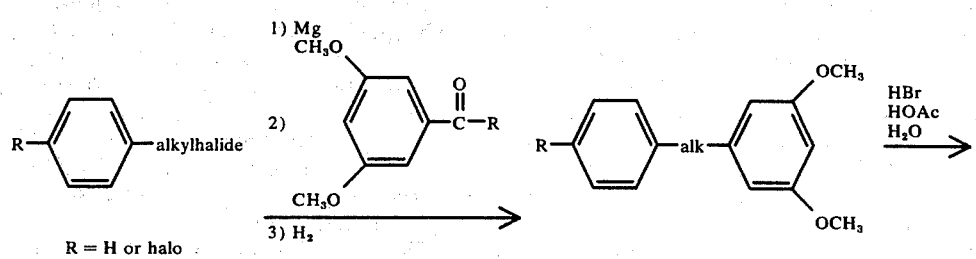

R = H or halo

-continued

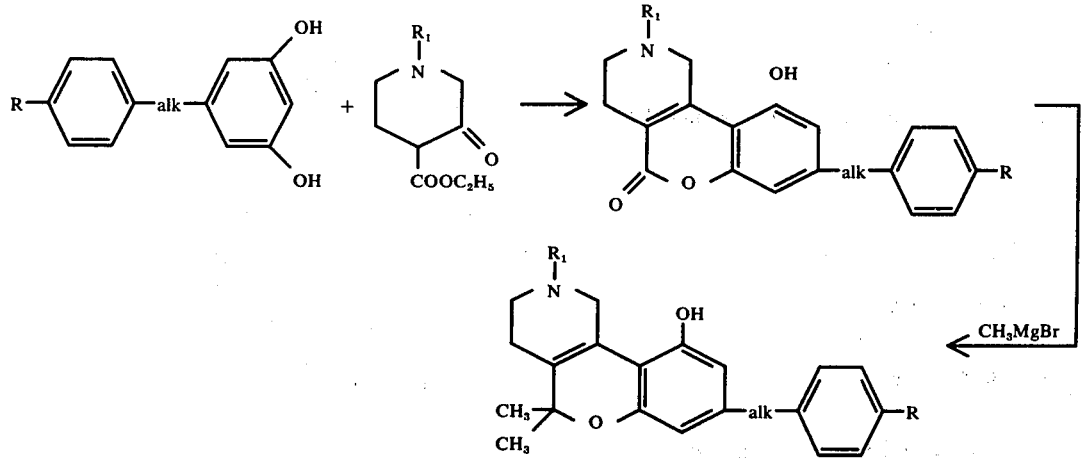

Compounds of formula II wherein $R_3$ is hydrogen and $R_4$ is alkyl or cycloalkyl can be prepared according to the method described in U.S. Pat. No. 3,576,798.

Compounds of formula X are prepared according to the method described in U.S. Pat. No. 2,419,937.

Compounds of formula XI are prepared according to the method described in U.S. Pat. No. 3,635,993.

Compounds of formula IX can be prepared according to the method described in U.S. Pat. No. 3,639,427.

Compounds of formula XII can be prepared according to the method described in U.S. Pat. No. 3,493,579.

Compounds of formulae III–XIII are prepared in a similar fashion using the appropriate β-keto ester. The methods are well described in the literature for a preparation of the starting materials, as well as the final products and are illustrated in the examples following:

The esters are prepared in identical fashion as are the esters of the above described compounds wherein $R_4$ is alkyl.

The following examples illustrate the preparation of compounds useful in the practice of this invention.

EXAMPLE 1

Preparation of 2-(3,5-dimethoxyphenyl)-5-(4-fluorophenyl)pentane

A solution of 77 g. of 3-(4-fluorophenyl)propylbromide in 300 ml. of ether was added dropwise over a 2 hour period to a refluxing solution of 10 g. of magnesium in 100 ml. of ether. The reaction mixture was refluxed for an additional 30 minutes after the addition was completed. A solution of 68 g. of 3,5-dimethoxyacetophenone in 100 ml. of ether was then added dropwise to the reaction and the reaction mixture was refluxed for 1½ hours. To the reaction was added 300 ml. of a saturated ammonium chloride solution dropwise with stirring. The layers were separated and the aqueous layer extracted with ether. The ether extract was dried over magnesium sulfate and the ether removed in vacuo to give an oil. An additional 111.7 g. of 3(4-fluorophenyl)propylbromide was worked up in the above manner. The products from both runs were hydrogenated in ethanol-HCl using palladium as the catalyst. The solvents and catalyst were removed and the crude material distilled to yield 169.0 g. of 2-(3,5-dimethoxyphenyl)-5-(4-fluorophenyl)pentane, b.p. 145–155/0.05 mmHg.

Analysis Calcd. for $C_{19}H_{23}O_2F$: C, 75.60; H, 7.69; found: C, 75.87; H, 7.98

EXAMPLE 2

Preparation of 2-(3,5-dihydroxyphenyl)-5-(4-fluorophenyl)pentane

Fifty grams of the above prepared 2-(3,5-dimethoxyphenyl)-5-(4-fluorophenyl)pentane, 450 ml. of acetic acid and 180 ml. of 48% HBr in water were mixed. While cooling, the mixture was saturated with hydrogen bromide gas (approximately one-half hour). The reaction was placed in an 87° bath and stirred for 17 hours. The reaction was then concentrated in vacuo and the residue neutralized with $K_2CO_3$ and $NaHCO_3$, extracted with ether, treated with charcoal and $MgSO_4$ and filtered to yield 45 g. of 2-(3,5-dihydroxyphenyl)-5-(4-fluorophenyl)pentane as a brown oil which distills at 180° /0.01 mmHg.

Analysis Calcd. for $C_{17}H_{25}O_2F$: C, 74.20; H, 6.98; Found: C, 73.56; H, 7.04

EXAMPLE 3

Preparation of 2-Benzyl-3-(4-fluorophenyl-1-methylbutyl)-10-hydroxy-5-oxo-1,2,3,4-tetrahydro-5H-[1]benzopyrano[3,4-d]pyridene hydrochloride To 45 g. of 2-(3,5-dihydroxyphenyl)-5-(4-fluorophenyl)pentane dissolved in 100 ml. of methanesulfonic acid were added in portions, 57 g. of 1-benzyl-3-keto-4-carbethoxy pyridene, hydrochloride. While stirring, 68 g. of $POCl_3$ were added and the solution was stirred for 5 days at room temperature. Water (300 ml.) and 180 ml. of $CHCl_3$ were then added and the reaction mixture stirred for 30 minutes. After the addition of 100 ml. of 15% of NaOH, the reaction was stirred for an additional ten minutes. The $CHCl_3$ layer was separated and extracted with 10% HCl. The $CHCl_3$ layer was concentrated and $CH_3CN$ added added thereto to yield 55 g. of the desired product as the hydrochloride salt, m.p. 254°–256° C.

Theory: C, 70.80; H, 6.14; Cl, 6.97; N, 2.75; Found: C, 70.15; H, 6.17; Cl, 7.23; N, 2.74

EXAMPLE 4

Preparation of 2-Benzyl-5,5-dimethyl-3-(4-fluorophenyl-1-methylbutyl)-10-hydroxy-1,2,3,4-tetrahydro-5H[l]benzopyrano[3,4-d]pyridene Sixty five grams of the above-prepared 2-Benzyl-3-(4-fluorophenyl-1-methylbutyl)-10-hydroxy-5-ono-1,2,3,4-tetrahydro-5H-[l]benzopyrano[3,4-d]pyridene hydrochloride were suspended in 300 ml. of $CHCl_3$. After adding a $KHCO_3$ solution, the reaction was stirred for 30 minutes. The chloroform layer was separated, dried over $MgSO_4$, concentrated, taken up in benzene and concentrated again. The concentrate was taken up in 185 ml. of hot anisole and the resulting solution was added dropwise to a solution of $CH_3MgBr$ in anisole (prepared by adding 180 g. of $CH_3Br$ in 500 ml. of ether to 40 g. of Mg in 150 ml. of ether, evaporating the ether and adding 300 ml. of anisole). The reaction mixture was stored overnight at 62° C. Water (200 ml.) was added slowly, followed by 400 ml. of 10% $H_2SO_4$. The anisole was removed by steam distillation and the resulting solid was taken up in chloroform, neutralized with $KHCO_3$, dried over $MgSO_4$, concentrated and the product (36.5 g.), m.p. 188°–190° C., crystallized from $CH_3CN$.

EXAMPLE 5

Preparation of 5,5-Dimethyl-8-(4-fluorophenyl-1-methylbutyl)-10-hydroxy-2-[3-(1-propynyl)]-1,2,3,4-tetrahydro-5H[l]benzopyrano[3,4-d]pyridine hydrochloride 32.8 g. of the above-prepared 2-Benzyl-5,5-dimethyl-3-(4-fluorophenyl-1-methylbutyl)-10-hydroxy-1,2,3,4-tetrahydro-5H[l]benzopyrano[3,4-d]pyridine was hydrogenated in ethanol. The catalyst was removed, the solution concentrated, and the desired product was crystallized from ethanol-Skelly B as 19.9 g. of amorphous solid, m.p. 222°–225° C.

Theory: C, 69.50; H, 7.23; N, 3.24; Cl, 8.21; Found: C, 69.67; H, 7.34; N, 3.12; Cl, 8.10

EXAMPLE 6

Preparation of 5,5-Dimethyl-8-(4-fluorophenyl-1-methylbutyl)-10-hydroxy-2-[3-(1-propynyl)]-1,2,3,4-tetrahydro-5H[l]benzopyrano[3,4-d]pyridine 5,5-Dimethyl-3-(4-fluorophenyl-1-methylbutyl)-10-hydroxy-1,2,3,4-tetrahydro-5H[l]benzopyrano[3,4-d]pyridine hydrochloride (19.9 g.) was dissolved in 88 ml. of dimethylformamide. While the solution was cooling, 3.14 g. of propargyl bromide were added. The reaction was stirred at room temperature for 15 hours. Water (120 ml.) was added slowly, whereupon the desired product crystallized. The crystalline product was washed with water and recrystallized from ether and $CH_3CN$ to yield 5.90 g. of the desired product, m.p. 164°–166° C.

Theory: C, 77.25; H, 7.46; N, 3.21; Found: C, 76.80; H, 7.76; N, 3.11

EXAMPLE 7

Preparation of 5,5-Dimethyl-8-(4-fluorophenyl-1-methylbutyl)-10-[4-(piperidino)butyryloxy]-2-(2-propynyl)-1,2,3,4-tetrahydro-5H/1/benzopyrano/3,4-d/pyridine hydrochloride 5,5-Dimethyl-8-(4-fluorophenyl-1-methylbutyl)-10-hydroxy-2-[3-(1-propynyl)]-1,2,3,4-tetrahydro-5H[l]benzopyrano[3,4-d]pyridine (4.528 g.) was dissolved in 125 ml. of methylene chloride and combined with 2.246 g. of γ-piperidinobutyric acid hydrochloride and 2.357 g. of dicyclohexylcarbodiimide (Cruickshank and Sheehan, J. Am. Chem. Soc., 83, 2891 (1961), m.p. 190°–192° C.). The reaction mixture was stirred at room temperature for 16 hours. The insoluble byproduct of dicyclohexylurea was separated by filtration and the methylene chloride was removed using a rotary evaporator. The residue was crystallized from 15 ml. of methylene chloride and 30 ml. of ether to yield 6.4 g. of the desired product as a white solid, m.p. 108°–119° C. (decomp.).

Theory: C, 71.29; H, 7.71; N, 4.49; Cl, 5.68; Found: C, 69.88; H, 7.92; N, 4.30; Cl, 6.59

NMR showed the presence of 1½% of methylene chloride in the product, which accounted for the analysis.

EXAMPLE 8

5,5-Dimethyl-10-[4-(morpholino)butyryloxy]-8-4-fluorophenyl-1-methylbutyl)-2-(2-propynyl)-1,2,3,4-tetrahydro-5H[1]benzopyrano[3,4-d]pyridine hydrochloride Equimolar amounts of 5,5-Dimethyl-10-hydroxy-8-(4-fluorophenyl-1-methylbutyl)-2-(2-propynyl)-1,2,3,4-tetrahydro-5H[1]benzopyrano[3,4-d]pyridine, γ-morpholinobutyric acid hydrochloride (Cruickshank and Sheehan, J.A.C.S. 83, 2891 (1961) and dicyclohexylcarbodiimide are combined in methylene chloride and stirred for 16 hours at room temperature. The insoluble by-product of dicyclohexylurea is removed by filtration and the methylene chloride is distilled off using a rotary evaporator. The residue is dissolved in a small amount of benzene and ether was added to give the crude product which can be recrystallized from methylene chloride/ligroin.

EXAMPLE 9

5,5-Dimethyl-10-[4-(2-methylpiperidino)butyryloxy]-8-(4-fluorophenyl-1-methylbutyl)-2-(2-propynyl)-1,2,3,4-tetrahydro-5H[1]benzopyrano[3,4-d]pyridine hydrochloride Methyl γ-(2-methylpiperidino) butyrate is dissolved in an 18% hydrochloric acid solution (90 ml. water and 90 ml. concentrated hydrochloric acid) and refluxed for 16 hours. The excess water is removed using reduced pressure (water aspirator) to give a semi-solid residue which is triturated with acetone and filtered to yield γ-(2-methylpiperidino) butyric acid hydrochloride as colorless crystals, m.p. 180°–182° C.

A mixture of equimolar quantities of 5,5-dimethyl-10-hydroxy-8-(4-fluorophenyl-1-methylbutyl)-2-(2-propynyl)-1,2,3,4-tetrahydro-5H[1]benzopyrano[3,4-d]pyridine, γ-(2-methylpiperidino)butyric acid hydrochloride and dicyclohexylcarbodiimide in methylene chloride are stirred at room temperature for 16 hours. The reaction mixture is cooled and the solid removed by suction filtration. The methylene chloride is evaporated to give a residue which is dissolved in methylene chloride and diethyl ether. After removing the resulting crude product, the solvents are evaporated and the gummy resin is dried, triturated with diethyl ether, and dried to yield the desired product.

EXAMPLE 10

5,5-Dimethyl-10-[5-(piperidono)valeryloxy]-8-(4-fluorophenyl-1-methylbutyl)-2-(2-propynyl)-1,2,3,4-tetrahydro-5H[1]benzopyrano[3,4-d]pyridine hydrochloride A mixture of 0.167 mole of methyl δ-chlorovalerate and 0.25 mole of sodium iodide in 120 ml. of acetone is stirred and heated at reflux for 16 hours. After cooling the mixture, a solid is removed by suction filtration, and the acetone is distilled off using a rotary evaporator. The residue is dissolved in 300 ml. of diethyl ether, and additional solid is removed by filtration. The ethereal solution is washed twice with a 10% sodium thiosulfate solution, one with water and dried over sodium sulfate. The ether is evaporated and the residue distilled at b.p. 107°–110° C. (15 mm.) to give 30.0 g. (74%) of methyl δ-iodovalerate as a light yellow liquid. 30.0 g. (0.124 mole) of methyl δ-iodovalerate and 42.5 g. (0.50 mole) of piperidine are dissolved in 250 ml. of benzene and heated at 60° C. for 3 hours with stirring. A colorless solid begins to appear shortly after the materials are combined. The solid is removed by suction filtration, and the benzene evaporated to give methyl δ-piperidinovalerate which distills as 23.5 g. (95%) of colorless liquid, b.p., 122°–24° C. (12.5 mm.).

23.5 g. (0.117 mole) of methyl δ-piperidinovalerate is dissolved in a combination of 125 ml. of concentrated hydrochloric acid and 125 ml. of water and refluxed with stirring for 16 hours. The excess water is removed using reduced pressure (water aspirator) to give a semi-solid residue which is triturated with acetone, filtered and dried. 21.0 g. (79%) of colorless crystals of δ-piperidinovaleric acid hydrochloride are obtained, m.p. of 202°–204° C.

A mixture of 2.4 g. (6.06 mm.) of 5,5-dimethyl-10-hydroxy-8-(4-fluorophenyl-1-methylbutyl)-2-(2-propynyl)-1,2,3,4-tetrahydro-5H[1]benzopyrano[3,4-d]pyridine, 1.35 g. (6.06 mm.) of δ-piperidinovaleric acid hydrochloride and 1.30 g. (6.30 mm.) of dicyclohexylcarbodiimide in 100 ml. of methylene chloride are stirred at room temperature for 5 hours. The reaction mixture is cooled overnight in the refrigerator and the by-product of dicyclohexylurea removed by suction filtration. The mother liquor is evaporated and the residue dissolved in a mixture of methylene chloride/cyclohexane and allowed to stand in the cold for 2 hours. Gravity filtration separates the small amount of solid which appears, and the solvents are removed using a rotary evaporator. Crystallization from methylene chloride/diethyl ether yields the desired product.

EXAMPLE 11

5,5-Dimethyl-10-[4-(pyrrolidino)butyryloxy]-8-3(4-fluorophenyl-n-pentyl)-2-(2-propynyl)-1,2,3,4-tetrahydro-5H [1]benzopyrano[3,4-d]pyridine dihydrochloride 30.0 g. (0.13 mole) of methyl γ-iodobutyrate [Blicke et al, *J. Am Chem. Soc.*, 63, 2488 (1941)] are combined with 36 g. (0.5 mole) of pyrrolidine in 300 ml. of benzene, heated at 60° C. for 0.5 hour and stirred at room temperature for 16 hours. A dark layer forms and the benzene solution is decanted, concentrated and distilled to give the crude product. This material is dissolved in a combination of 50 ml. of concentrated hydrochloric acid and 50 ml. of water and heated at reflux for 28 hours. The solution is concentrated under reduced pressure to give a semi-solid residue which is triturated with acetone and filtered. Recrystallization from a combination of 11 ml. of acetic acid/40 ml. of acetone yields 8.3 g. (33%) of colorless crystals of γ-pyrrolidinobutyric acid hydrochloride, m.p. 126°–127° C.

3.0 g. (7.57 mm.) of 5,5-dimethyl-10-hydroxy-8-(4-fluorophenyl-n-pentyl)-2-(2-propynyl)-1,2,3,4-tetrahydro-5H[1]benzopyran[3,4-d]pyridine is combined with 1.45 g. (7.57 mm.) of γ-pyrrolidinobutyric acid hydrochloride and 1.67 g. (8.12 mm.) of dicyclohexylcarbodiimide in 150 ml. of methylene chloride and stirred at room temperature for 3 hours. The reaction mixture is stored for 16 hours in the cold, and the by-product of dicyclohexylurea removed by suction filtration. After evaporation of the solvents, the resulting residue is dissolved and allowed to stand at room temperature for 2 hours and at 5° C. for 16 hours. A small quantity of solids is separated by gravity filtration, and the solvents are removed on a rotary evaporator. Crystallization from methylene chloride and diethyl ether give the desired product as the dihydrochloride.

EXAMPLE 12

5,5-Dimethyl-10-[4-(piperidino)butyryloxy]-2-(2-propynyl)-8-(1-methyl butylphenyl)-1,2,3,4-tetrahydro-5H[1]benzopyrano [3,4-d]pyridine hydrochloride A mixture of 1.45 g. (4.26 mm) of 5,5-dimethyl-10-hydroxy-2-(2-propynyl)-8-(1-methylbutylphenyl)-1,2,3,4-tetrahydro-5H[1]benzopyrano[3,4-d]pyridine, 0.89 g. (4.28 mm.) of Δ-piperidinobutyric acid hydrochloride and 0.93 g. (4.50 mm.) of dicyclohexylcarbodiimide in 200 ml. of methylene chloride are stirred at room temperature for 18 hours. After cooling the reaction mixture for 1½ hours, the by-product of dicyclohexylurea is removed by suction filtration. A rotary evaporator is used to remove the methylene chloride, and a mixture of 25 ml. of methylene chloride and 50 ml. of cyclohexane is added. After standing at room temperature for 2 hours and a 5° C. for 16 hours, gravity filtration is used to separate the resulting solid. This material is generally a mixture of the starting acid hydrochloride and the hydrochloride salt of the starting benzopyran. The mother liquid is evaporated and the residue crystallized from a mixture of 2 ml. of methylene chloride and 15 ml. of diethyl ether. After filtration and drying, the pure product is obtained.

EXAMPLE 13

5,5-Dimethyl-8-(ethylphenyl)-10-[4-(piperidino)-butyryloxy]-2-(2-propynyl)-1,2,3,4-tetrahydro-5H[1]benzopyrano [3,4-d]pyridine hydrochloride Equimolar quantities of 5,5-dimethyl-10-hydroxy-8-(ethylphenyl)-2-(2-propynyl)-1,2,3,4-tetrahydro-5H[1]benzopyran, dicyclohexylcarbodiimide and γ-piperidinobutyric acid hydrochloride are combined in methylene chloride. After stirring for about 16 hours at room temperature, the reaction mixture was cooled, and the by-product of dicyclohexylurea is removed by suction filtration. The mother liquor is evaporated to give a residue which is dissolved in a methylene chloride/cyclohexane mixture and stored in the cold for 16 hours. A small quantity of additional dicyclohexylurea is removed by filtration, and the solvents are distilled off using a rotary evaporator. The residue which remained is dried in vacuo and crystallized from a mixture of methylene chloride and diethyl ether to give the desired product. A second crop of material can be obtained by workup of the mother liquor.

EXAMPLE 14

5,5-Dimethyl-10-[2-methyl-4-(piperidino)butyryloxy]-8-(4-fluorophenyl-1-methylbutyl)-2-(2-propynyl)-1,2,3,4-tetrahydro-5H[1]benzopyrano[3,4-d]pyridine hydrochloride The method of Lee V. Phillips (U.S. Pat. No. 3,299,100) is used to prepare α-methyl-γ-butyrolacetone and this material is converted to ethyl γ-bromo-α-methylbutyrate via the procedure of G. Jones and J. Wood, "The Synthesis of 9-Azasteroids-II", Tetrahedron, 21, 2961 (1965).

10.5 g. (0.05 mole) of ethyl γ-bromo-α-methylbutyrate is combined with 17.0 g. (0.20 mole) of piperidine and 100 ml. of benzene, stirred for 16 hours at room temperature and heated at 60° C. for 4 hours. The reaction mixture is cooled and the colorless solid which appeared is removed by filtration. The mother liquor is concentrated to give ethyl α-methyl-γ-piperidinobutyrate as a mobile yellow liquid which distills (b.p. 78° at 0.25 mm.) as 6.7 g. (63%) of colorless liquid.

6.5 g. (0.030 mole) of ethyl α-methyl-γ-piperidinobutyrate are combined with a mixture of 45 ml. of water and 45 ml. of concentrated hydrochloric acid and heated at reflux for 16 hours. The solution is concentrated under reduced pressure (water aspirator) to give a residue which crystallizes upon addition of 50 ml. of diethyl ether. The ether is decanted, and the solid was triturated with acetone and filtered. Recrystallization from acetic acid/acetone gives 3.38 g. of α-methyl-γpiperidinobutyric acid hydrochloride as colorless crystals, m.p. 166°–68° C. and a second crop of 1.27 g. of solid, m.p. 165°–168° C. The total yield for both batches is 69%. The nuclear magnetic resonance and infrared spectra are in agreement with the proposed structure.

2.0 g. (5.05 mm.) of 5,5-dimethyl-10-hydroxy-8-(4-fluororophenyl-1-methylbutyl)-2-(2-propynyl)-1,2,3,4-tetrahydro-5H[1]benzopyrano[3,4-d]pyridine are combed with 1.12 g. (5.05 mm.) of α-methyl-γ-piperidino butyric acid hydrochloride and 1.08 g. (5.25 mm.) of dicyclohexylcarbodiimide in 110 ml. of methylene chloride and the mixture is stirred at room temperature for 16 hours. After cooling for 4 hours, the by-product of dicyclohexylurea is removed by suction filtration. The mother liquor is evaporated to give a colorless foamy residue which is dissolved in a methylene chloride/cyclohexane mixture and stored for 16 hours in the cold. A small amount of solid is separated by gravity filtration, and the solvents are removed using a rotary evaporator. The residue is dried to give a colorless solid which is dissolved in a mixture of methylene chloride/diethyl ether and converted to the dihydrochloride by the addition of a solution of hydrogen chloride is diethyl ether. The solvents are decanted, and the gummy residue crystallized upon trituration with diethyl ether. The solid is filtered and recrystallized from 20 ml. of methylene chloride/20 ml. diethyl ether to give the desired product.

EXAMPLE 15

5,5-Dimethyl-10-[4-(morpholino)butyryloxy]-8-(4-fluorophenyl-1-methylbutyl)-2-(2-propynyl)-1,2,3,4-tetrahydro-5H[1]benzopyrano[3,4-d]pyridine dihydrochloride 4.0 g. (10.1 mm.) of 5,5-dimethyl-10-hydroxy-8-(4-fluorophenyl-1-methylbutyl)-2-(2-propynyl)-1,2,3,4-tetrahydro-5H[1]benzopyrano[3,4-d]pyridine, 2.10 g. (10.1 mm.) of γ-morpholino-butyric acid hydrochloride and 2.18 g. (10.6 mm.) of dicyclohexylcarbodiimide are added to 200 ml. of methylene chloride. The reaction mixture is stirred at room temperature for 16 hours and after cooling, the by-product of dicyclohexylurea is removed by suction filtration. The mother liquor is evaporated to give a residue, which, after the usual workup, is converted to a dihydrochloride by the addition of an ether solution of hydrogen chloride. Recrystallization from methylene chloride/diethyl ether gives the final product.

EXAMPLE 16

5,5-Dimethyl-10-[3-(piperidino)propionyloxy]-8-(methylphenyl)-2-(2-propynyl)-1,2,3,4-tetrahydro-5H[1]benzopyrano[3,4-d]pyridine tartrate 5,5-Dimethyl-10-hydroxy-8-(methylphenyl)-2-(2-propynyl)-1,2,3,4-tetrahydro-5H[1]benzopyrano[3,4-d]pyridine (1 mm.), dicyclohexylcarbodiimide (1 mm.) and β-piperidinopropionic acid (1 mm.) are combined in 30 ml. of methylene chloride and stirred for 16 hours. The insoluble by-product of dicyclohexylurea is removed by filtration and the methylene chloride is distilled off using a rotary evaporator. The residue is dissolved in benzene and filtered to remove any insoluble material. The solvent is evaporated and the residue is chromatographed to yield the desired product as neutral material which can be converted to the tartrate by well known methods.

The following compoundas are prepared according to the method of Example 16 by reacting the desired benzopyranopyridine with the appropriate acid or acid salt.

EXAMPLE 17

5,5-Dimethyl-8-(4-fluorophenyl-1-methylbutyl)-2-(2-propynyl)-1,2,3,4-tetrahydro-10-[4-(thiomorpholino)-butyryloxy]-5H[1] benzopyrano[3,4-d]pyridine hydrobromide Equimolar amounts of 5,5dimethyl-10-hydroxy-8-(4-fluorophenyl-1-methylbutyl)-2-(2-propynyl)-1,2,3,4-tetrahydro-5H[1]benzopyrano[3,4-d]pyridine, γ-thiomorpholinobutyric acid hydrobromide and dicyclohexylcarbodiimide are reacted to form the desired product.

EXAMPLE 18

5,5-Dimethyl-2-benzyl-10-[2-(homopiperidino)acetoxy]-8-(4-fluorophenyl-n-hexyl)-1,2,3,4-tetrahydro-5H[1]benzopyrano[3,4-d]pyridine Equimolar amounts of 5,5-dimethyl-2-benzyl-8-(4-fluorophenyl-n-hexyl)-10-hydroxy-1,2,3,4-tetrahydro-5H[1] benzopyrano[3,4-d]pyridine, homopiperidinoacetic acid and dicyclohexylcarbodiimide are reacted to form the desired product.

EXAMPLE 19

5,5-Dimethyl-10-[4-(moropholino)butyryloxy]-8-(3,4-difluorophenyl-n-pentyl)-2-methyl-1,2,3,4-tetrahydro-5H[1]benzopyrano[3,4-d]pyridine hydrochloride 5,5-Dimethyl-10-hydroxy-8-(3,4-difluorophenyl-n-pentyl)-1,2,3,4-tetrahydro-5H[1]benzopyrano[3,4-d]pyridine, γ-morpholino-butyric acid hydrochloride and dicyclohexylcarbodiimide are combined in equimolar amounts in methylene chloride and reacted as in Example 7 to give the desired product.

EXAMPLE 20

2-Benzyl-5,5-diethyl-10-[4-(morpholino)butyryloxy]-8-2,5-difluorophenyl-n-octyl-1,2,3,4-tetrahydro-5H[1]benzopyrano[3,4-d]pyridine hydrochloride 2-Benzyl-5,5-dimethyl-10-hydroxy-8-(2,5-difluorophenyl-n-octyl)-1,2,3,4-tetrahydro-5H[1]benzopyrano[3,4-d] pyridine, γ-morpholino-butyric acid hydrochloride and dicyclohexylcarbodiimide are combined in equimolar amounts in methylene chloride and reacted as in Example 7 to give the desired product.

EXAMPLE 21

2-Benzyl-5,5-dimethyl-10-[4-(2-methylpiperidino)-butyryloxy]-8-(2-methyl-5-chlorophenyl-1-methylbutyl)-1,2,3,4-tetrahydro-5H[1]benzopyrano[3,4-d]pyridine hydrochloride 2-Benzyl-5,5-dimethyl-10-hydroxy-8-(2-methyl-5-chlorophenyl-1-methylbutyl)-1,2,3,4-tetrahydro-5H[1]benzopyrano[3,4-d]pyridine, γ-(2-methylpiperidino)-butyric acid hydrochloride and dicyclohexylcarbodiimide in equimolar amounts are reacted as in Example 7 to give the desired product.

EXAMPLE 22

5,5-Dimethyl-10-[4-(pyrrolidino)butyryloxy]-2-phenethyl-8-(4-chlorophenyl-1-methylbutyl)-1,2,3,4-tetrahydro-5H [1]benzopyrano[3,4-d]pyridine hydrochloride 5,5-Dimethyl-10-hydroxy-2-phenethyl-8-(4-chlorophenyl-1-methylbutyl)-1,2,3,4-tetrahydro-5H[1]benzopyrano [3,4-d]pyridine, γ-pyrrolidinobutyric acid hydrochloride and dicyclohexylcarbodiimide are reacted in equimolar amounts according to Example 7 to produce the desired product.

EXAMPLE 23

2-Allyl-5,5-dimethyl-8-(4-fluorophenyl-1-methylbutyl)-10-[4-(piperidino)butyryloxy]-1,2,3,4-tetrahydro-5H[1]benzopyrano[3,4-d]pyridine hydrochloride 2-Allyl-5,5-diethyl-8-(4-fluorophenyl-1-methylphenyl)-10-hydroxy-1,2,3,4-tetrahydro-5H[1]benzopyrano[3,4-d]pyridine, γ-piperidinobutyric acid hydrochloride and dicyclohexylcarbodiimide are reacted and in equimolar amounts to produce the desired product.

EXAMPLE 24

2-(2-Cyclohexylethyl)-5,5-dimethyl-8-(4-fluorophenyl-1-methylphenyl)-10-[5-(morpholino)valeryloxy]-1,2,3,4-tetrahydro-5H[1]benzopyrano[3,4-d]pyridine hydrochloride 2-(2-Cyclohexylethyl)-5,5-dimethyl-10-hydroxy-8-(4-fluorophenyl-1-methylphenyl)-1,2,3,4-tetrahydro-5H[1] benzopyrano[3,4-d]pyridine, δ-piperidinovaleric acid hydrochloride and dicyclohexylcarbodiimide are reacted in equimolar amounts according to Example 7 to form the desired product.

EXAMPLE 25

2-Cinnamyl-8-(2,3-dimethylphenyl-n-heptyl)-5,5-di(n-propyl)-10-[4-pyrrolidino)butyryloxy]-1,2,3,4-tetrahydro-5H[1]benzopyrano[3,4-d]pyridine hydrochloride 2-Cinnamyl-8-(2,3-dimethylphenyl-n-heptyl)-5,5-di(n-propyl)-10-hydroxy-1,2,3,4-tetrahydro-5H[1]benzopyrano [3,4-d]pyridine, γ-pyrrolidinobutyric acid hydrochloride and dicyclohexylcarbodiimide are reacted in equimolar amounts according to Example 1 to form the desired product.

EXAMPLE 26

5,5-Dimethyl-8-(3-methyl-2-octyl)-10-[4-(piperidino)butyryloxy]-2-(2-propynyl)-1,2,3,4-tetrahydro-5H[1]benzopyrano[3,4-d]pyridine hydrochloride (SP-106)

4.5 g. (11.4 mm.) of 5,5-Dimethyl-10-hydroxy-8-(3-methyl-2-octyl)-2-(2-propynyl)-1,2,3,4-tetrahydro-5H-[1]benzopyrano[3,4-d]pyridine, 2.58 g. (12.5 mm.) of cicyclohexylcarbodiimide and 2.49 g. (12.0 mm.) of γ-piperidinobutyric acid hydrochloride (Cruickshank and Sheehan, J. Am. Chem. Soc., 83, 2891 (1961) m.p. 190°–192° C.) were combined in 250 ml. of methylene chloride and stirred at room temperature for 16 hours. The insoluble by-product of dicyclohexylurea was separated by filtration and the methylene chloride was removed using a rotary evaporator. The residue was dissolved in benzene or benzene/cyclohexane mixtures and filtered several times to remove a small amount of insoluble material. The solvent was evaporated and the residue was dissolved in water and lyophilized to give 2.3 g. (37%) of product as a light yellow solid.

The material showed on $R_f$ of 0.5 in thin layer chromatography (10% MeOH/CHCl$_3$); the infrared and nuclear magnetic resonance spectra were in agreement with the proposed structure.

Analysis Calcd. for $C_{35}H_{53}ClN_2O_3 \cdot 2½\ H_2O$ (MW=630.27): C, 66.70; H, 9.29; N, 4.46; Found: C, 66.58; H, 8.93; N, 4.54

EXAMPLE 27

5,5-Dimethyl-10-[4-(morpholino)butyryloxy]-8-(3-methyl-2-octyl)-2-(2-propynyl)-1,2,3,4-tetrahydro-5H-[1]-benzopyrano [3,4-d] pyridine hydrochloride (SP-112)

0.6 g. (1.51 mm.) of 5,5-Dimethyl-10-hydroxy-8-(3-methyl-2 -octyl)-2-(2-propynyl)-1,2,3,4-tetrahydro-5H-[1]benzopyrano [3,4-d]pyridine, 0.317 g. (1.51 mm.) of γ-morpholinobutyric acid hydrochloride (Cruickshank and Sheehan, J.A.C.S. 83, 2891 (1961) and 0.34 g. (1.65 mm.) of dicyclohexylcarbodiimide were combined in 40 ml. of methylene chloride and stirred for 16 hours at room temperature. The insoluble by-product of dicyclohexylurea was removed by filtration of the methylene chloride was distilled off using a rotary evaporator. The residue was dissolved in a small amount of benzene and ether was added to give 0.4 g. of material. Recrystallization from methylene chloride/ligroin (b.p. 100°–115° C) gave 0.3 g. (31%) of product as a beige solid, mp. 158°–161° C. The sample was found pure by thin layer chromatography (20% MeOH/CHCl$_3$). The infrared and nuclear magnetic resonance spectra and consistent with the proposed structure.

Analysis Calcd. for $C_{34}H_{51}ClN_2O_4 \cdot 2\text{-}1/2$ $H_2O$ (MW=632.26): C, 64.60; H, 8.93; N, 4.43; Found: C, 64.32; H, 8.54; N, 4.31

EXAMPLE 28

5,5-Dimethyl-10-[4-(2-methylpiperidino) butyryloxy]-8-(3-methyl-2-octyl)-2-(2-propynyl)-1,2,3,4-tetrahydro-5H-[1]benzopyrano [3,4-d] pyridine hydrochloride (SP-159)

14.0 g. (0.07 mole) of methyl γ-(2-methylpiperidino) butyrate was dissolved in 180 ml. of 18% hydrochloric acid solution (90 ml. water and 90 ml. concentrated hydrochloric acid) and refluxed for 16 hours. The excess water was removed using reduced pressure (water aspirator) to give a semi-solid residue which was triturated with acetone and filtered. 11.3 g. (73%) of γ-(2-methylpiperidino) butyric acid hydrochloride was obtained as colorless crystals, m.p. 180°–182° C.

A mixture of 3.0 g. (7.6 mm.) of 5,5-dimethyl-10-hydroxy-8-(3-methyl-2-octyl)-2-(2-propynyl)-1,2,3,4-tetrahydro-5H-[1] benzopyrano [3,4-d]pyridine, 1.68 g. (7.6 mm.) of γ-(2-methylpiperidino)butyric acid hydrochloride and 1.65 g. (8.0 mm.) of dicyclohexylcarbodiimide in 150 ml. of methylene chloride was stirred at room temperature for 16 hours. The reaction mixture was cooled and the solid removed by suction filtration. The methylene chloride was evaporated to give a residue which was dissolved in 8 ml. of methylene chloride and 58 ml. diethyl ether. After standing for 3 days, a total of 100 mg. of solid was removed by gravity filtration. The solvents were evaporated and the gummy resin was dried to give a foam-like residue which was triterated with 30 ml. of diethyl ether. The resulting nearly colorless, gummy residue was dried to give 2.8 g. (61%) of tan solid.

The sample was pure of thin layer chromatography (5% MeOH/ChCl$_3$); the infrared and nuclear magnetic resonance spectra were in agreement with the proposed structure.

Analysis Calcd. for $C_{36}H_{55}cin_2O_3$ (MW=599.28): C, 72.14; H, 9.25; N, 4.67; Found: C, 71.94; H, 9.16; N, 4.58

EXAMPLE 29

5,5-Dimethyl-10-[5-(piperidino)valeryloxy]-8(3-methyl-2-octyl)-2-(2-propynyl)-1,2,3,4-tetrahydro-5H-[1]benzopyrano[3,4-d] pyridine hydrochloride (SP-158)

A mixture of 25.0 g. (0.167 mole) of methyl δ-chlorovalerate and 37.5 g. (0.25 mole) of sodium iodide in 120 ml. of acetone was stirred and heated at reflux for 16 hours. After cooling the mixture, a solid was removed by suction filtration, and the acetone was distilled off using a rotary evaporator. The residue was dissolved in 300 ml. of diethyl ether, and additional solid was removed by filtration. The ethereal solution was washed twice with a 10% sodium thiosulfate solution once with water and dried over sodium sulfate. The ether was evaporated and the residue was distilled at b.p. 107°–110° C (15 mm.) to give 30.0 g. (74%) of methyl δ-iodovalerate as a light yellow liquid.

30.0 g. (0.124 mole) of methyl δ-iodovalerate and 42.5 g. (0.50 mole) of piperidine were dissolved in 250 ml. of benzene and heated at 60° C for 3 hours with stirring. A colorless solid began to appear shortly after the materials were combined. The solid was removed by suction filtration, and the benzene evaporated to give methyl δ-piperidinovalerate which distilled as 23.5 g. (95%) of colorless liquid, b.p. 122°–24° C (12.5 mm.).

23.5 g. (0.117 mole) of methyl δ-piperidinovalerate was dissolved in a combination of 125 ml. of concentrated hydrochloric acid and 125 ml. of water and refluxed with stirring for 16 hours. The excess water was removed using reduced pressure (water aspirator) to give a semi-solid residue which was triturated with acetone, filtered and dried. 21.0 g (79%) of colorless crystals of δ-piperidinovaleric acid hydrochloride was obtained with a m.p. of 202°–204° C.

A mixture of 2.4 g. (6.06 mm.) of 5,5-dimethyl-10-hydroxy-8-(3-methyl-2-octyl)-2-(2-propynyl)-1,2,3,4-tetrahydro-5H-[1]benzopyrano[3,4-a]pyridine, 1.35 g. (6.06 mm.) of δ-piperidinovaleric acid hydrochloride and 1.30 g. (6.30 mm.) of dicyclohexylcarbodiimide in 100 ml. of methylene chloride was stirred at room temperature for 5 hours. The reaction mixture was cooled overnight in the refrigerator and the byproduct of dicyclohexylurea removed by suction filtration. The mother liquor was evaporated to give a golden, viscous residue which was dissolved in a mixture of methylene chloride/cyclohexane and allowed to stand in the cold for 2 hours. Gravity filtration separated a small amount of solid which had appeared, and the solvents were removed using a rotary evaporator. Crystallization from methylene chloride/diethyl ether gave 2.5 g. (69%) of colorless crystals, m.p. 140°–144° C. The sample was pure by thin layer chromatography (10% MeOH/CHCl$_3$) and the infrared and nuclear magnetic resonance spectra were in agreement with the proposed structure.

Analysis Calcd. for $C_{36}H_{55}ClN_2O_3$ (MW=599.28). C, 72.14; H, 9.25; N, 4.67; Found: C, 72.00; H, 9.11; N, 4.63

EXAMPLE 30

5,5-Dimethyl-10-[4-pyrrolidino)butyryloxy]-8-3(3-methyl-2-octyl)-2-(2-propynyl)-1,2,3,4-tetrahydro-5H-[1]benzopyrano[3,4-d]pyridine dihydrochloride (SP-167)

30.0 g. (0.13 mole) of methyl γ-iodobutyrate [Blicke et al, *J. Am Chem. Soc*, 63, 2488 (1941)] was combined with 36 g (0.5 mole) of pyrrolidine in 300 ml. of benzene and heated at 60° C for 0.5 hour and stirred at room temperature for 16 hours. A dark orange layer formed, and the benzene solution was decanted, concentrated and distilled to give 10 g. of colorless liquid. This material was dissolved in a combination of 50 ml. of concentrated hydrochloric acid and 50 ml. of water and heated at reflux for 28 hours. The solution was concentrated under reduced pressure to give a semi-solid residue which was triturated with acetone and filtered. Recrystallization from a combination of 11 ml.

of acetic acid/40 ml. of acetone gave 8.3 g (33%) of colorless crystals of γ-pyrrolidinobutyric acid hydrochloride, m.p. 126°–127° C.

3.0 g. (7.57 mm.) of 5,5-dimethyl-10-hydroxy-8-(3-methyl-2-octyl)-2-(2-propynyl)-1,2,3,4-tetrahydro-5H[1]benzopyran [3,4-d]pyridine was combined with 1.45 g. (7.57 mm.) of γ-pyrrolidinobutyric acid hydrochloride and 1.67 g. (8.12 mm.) of dicyclohexylcarbodiimide in 150 ml. of methylene chloride and stirred at room temperature for 3 hours. The reaction mixture was stored for 16 hours in the cold, and the byproduct of dicyclohexylurea was removed by suction filtration. After evaporation of the solvents, the resulting gummy residue was dissolved in a mixture of 25 ml. methylene chloride and 65 ml. of cyclohexane and allowed to stand at room temperature for 2 hours and at 5° C for 16 hours. A small quantity of solid was separated by gravity filtration, and the solvents were removed on a rotary evaporator. Crystallation from methylene chloride and diethyl ether gave 0.75 g. (16%) of the desired product as the dihydrochloride, a colorless solid having a melting point of 168°–171° C which was pure by thin layer chromatography (10% MeOH/CHCl$_3$). The infrared and nuclear magnetic reasonance spectra were in agreement with the proposed structure.

Analysis Calcd. for $C_{34}H_{52}Cl_2N_2O_3 \cdot H_2O$ (MW=624.70): C, 65.35; H, 8.54; N, 4.48; Found: C, 65.24; H, 8.32; N, 4.58

EXAMPLE 31

5,5-Dimethyl-10-[4-(piperidino)butyryloxy]-2-(2-propynyl)-8-pentyl-1,2,3,4-tetrahydro-5H-[1]benzopyrano[3,4-d]pyridine hydrochloride (SP-171)

A mixture of 1.45 g. (4.26 mm.) of 5,5-dimethyl-10-hydroxy-2-(2-propynyl)-8-pentyl-1,2,3,4-tetrahydro-5H-[1]benzopyrano[3,4-d]pyridine, 0.89 g. (4.28 mm.) of γ-piperidinobutyric acid hydrochloride and 0.93 g. (4.50 mm.) of dicyclohexylcarbodiimide in 200 ml. of methylene chloride was stirred at room temperature for 18 hours. After cooling the reaction mixture for 1 ½ hours, the byproduct of dicyclohexylurea was removed by suction filtration. A rotary evaporator was used to remove the methylene chloride, and a mixture of 25 ml. of methylene chloride and 50 ml. of cyclohexane was added. After standing at room temperature for 2 hours and a 5° C for 16 hours, gravity filtration was used to separate 300 mg. of solid. This material proved to be a mixture of the starting acid hydrochloride and the hydrochloride salt of the starting benzopyran. The mother liquor was evaporated and the residue was crystallized from a mixture of 2 ml. of methylene chloride and 15 ml. of diethyl ether. After filtration and drying, a total of 0.5 g. (22%) of colorless solid was obtained. The sample was pure by thin layer chromatography (10% MeOH/CHCl$_3$). The infrared and nuclear magnetic resonance spectra were in agreement with the proposed structure.

Analysis Calcd. for $C_{31}H_{45}ClN_2O_3 \cdot 1/2H_2O$ (MW=538.15): C, 69.18; H, 8.61; N, 5.20; Found: C, 69.08; H, 8.74; N, 5.20

EXAMPLE 32

5,5-Dimethyl-8-(3-methyl-2-octyl)-10-[4-(piperidino)-butyryloxy]-2-(2-propynyl)-1,2,3,4-tetrahydro-5H-[1]benzopyrano[3,4-d]pyridine hydrochloride (SP-106)

The preparation of this compound was repeated by combining equimolar quantities of 5,5-dimethyl-10-hydroxy-8-(3-methyl-2-octyl)-2-(2-propynyl)-1,2,3,4-tetrahydro-5H-[1]benzopyran, dicyclohexylcarbodiimide and γ-piperidinobutyric acid hydrochloride in methylene chloride. After stirring for about 16 hours at room temperature, the reaction mixture was cooled, and the byproduct of dicyclohexylurea was removed by suction filtration. The mother liquor was evaporated to give a light yellow residue which was dissolved in a methylene chloride/cyclohexane mixture and stored in the cold for 16 hours. A small quantity of additional dicyclohexylurea was removed by filtration, and the solvents were distilled off using a rotary evaporator. The residue which remained was dried in vacuo and crystallized from a mixture of methylene chloride and diethyl ether to give a colorless solid, m.p. 108°–111° C. Thin layer chromatography (10% MeOH/CHCl$_3$) indicated the compound to be pure; the nuclear magnetic resonance and infrared spectra of the material were consistent with the desired product.

Analysis Calcd. for $C_{35}H_{53}ClN_2O_3$ (MW=585.24) C, 71.80; H, 9.12; N, 4.78; Found: C, 71.82; H, 9.17; N, 4.85

A second crop of material was obtained by workup of the mother liquor, and this material appeared similar to the main batch in all ways.

Analysis: Found: C, 71.66; H, 9.05; N, 4.76
Total yield for both batches was 95%.

EXAMPLE 33

5,5-Dimethyl-10-[2-methyl-4-(piperidino)butyryloxy]-8-(3-methyl-2-octyl)-2-(2-propynyl)-1,2,3,4-tetrahydro-5H-[1]benzopyrano[3,4-d] pyridine dihydrochloride (SP-178)

The method of Lee V. Phillips (U.S. Pat. No. 3,299,100) was used to prepare α-methyl-γ-butyrolactone and this material was converted to ethyl γ-bromo-α-methylbutyrate via the procedure of G. Jones and J. Wood, "The Synthesis of 9-Azasteroids-II", Tetrahedron, 21, 2961 (1965).

10.5 g. (0.05 mole) of ethyl γ-bromo-α-methylbutyrate was combined with 17.0 g. (0.20 mole) of piperidine and 100 ml. of benzene and stirred for 16 hours at room temperature and heated at 60° C for 4 hours. The reaction mixture was cooled and the colorless solid which appeared was removed by filtration. The mother liquor was concentrated to give ethyl α-methyl-γ-piperidinobutyrate as a mobile yellow liquid which distilled (b.p. 78° C at 0.25 mm.) as 6.7 g. (63%) of colorless liquid. The nuclear magnetic resonance and infrared spectra were consistent with the desired compound.

6.5 g. (0.030 mole) of ethyl α-methyl-γ-piperidinobutyrate was combined with a mixture of 45 ml. of water and 45 ml. of concentrated hydrochloric acid and heated at reflux for 16 hours. The solution was concentrated under reduced pressure (water aspirator ) to give a residue which crystallized upon addition of 50 ml. of diethyl ether. The ether was decanted, and the solid was triturated with acetone and filtered. Recrystallization from acetic acid/acetone gave 3.38 g. of α-methyl-γ-piperidinobutyric acid hydrochloride as colorless crystals, m.p. 166°–68° C and a second crop of 1.27 g. of solid, m.p. 165°–168° C. The total yield for both batches was 69%. The nuclear magnetic resonance and infrared spectra were in agreement with the proposed structure.

2.0 g. (5.05 mm.) of 5,5-dimethyl-10-hydroxy--8-(3-methyl-2-octyl)-2-(2-propynyl)-1,2,3,4-tetrahydro-5H[1] benzopyrano[3,4-d] pyridine was combined with 1.12 g. (5.05 mm.) of α-methyl-γ-piperidino butyric acid hydrochloride, and 1.08 g. (5.25 mm.) of dicyclohexylcarbodiimide in 110 ml. of methylene chloride and the mixture was stirred at room temperature for 16 hours. After cooling for 4 hours, the by-product of dicyclohexylurea was removed by suction filtration. The mother liquor was evaporated to give a colorless foamy residue which was dissolved in a methylene chloride/cyclohexane mixture and stored for 16 hours in the cold. A small amount of solid was separated by gravity filtration, and the solvents were removed using a rotary evaporator. The residue was dried to give 2.6 g. of colorless solid which was combined with 0.6 g. of material obtained from an earlier preparation. Both samples were dissolved in a mixture of methylene chloride/diethyl ether and converted to the dihydrochloride by the addition of a solution of hydrogen chloride in diethyl ether. The solvents were decanted, and the gummy residue crystallized upon trituration with diethyl ether. The solid was filtered and recrystallized from 20 ml. of methylene chloride/20 ml. diethyl ether to give 1.7 g. of 5,5-dimethyl-10-[2-methyl-4-(piperidino)butyryloxy]-8-(3-methyl-2-octyl)-2-(2-propynyl)-1,2,3,4-tetrahydro-5H-[1] benzopyrano [3,4-d]pyridine dihydrochloride as colorless crystals, m.p. 175°–80° C. The nuclear magnetic resonance and infrared spectra were consistent with the desired structure, and the material was pure by thin layer chromatography (10% MeOH/CHCl$_3$).

Analysis Calcd. for $C_{36}H_{58}Cl_2N_2O_3$ (MW=635.74); Theory: C, 68.00; H, 8.88; N, 4.41; Found: C, 67.96; H, 8.70; N, 4.34

EXAMPLE 34

5,5-Dimethyl-10-[4-(morpholino)butyryloxy]-8-(3-methyl-2-octyl)-2-(2-propynyl)-1,2,3,4-tetrahydro-5H-[1]benzopyrano[3,4-d] pyridine dihydrochloride (SP-112)

4.0 g. (10.1 mm.) of 5,5-dimethyl-10-hydroxy-8-(3-methyl-2-octyl)-2-(2-propynyl-1,2,3,4-tetrahydro-5H-[1] benzopyrano [3,4-d]pyridine, 2.10 g. (10.1 mm.) of γ-morpholinobutyric acid hydrochloride and 2.18 g. (10.6 mm.) of dicyclohexylcarbodiimide were added to 200 ml. of methylene chloride. The reaction mixture was stirred at room temperature for 16 hours and after cooling the byproduct of dicyclohexyurea was removed by suction filtration. The mother liquor was evaporated to give a residue which after the usual workup was converted to a dihydrochloride by the addition of an ether solution of hydrogen chloride. Recrystallization from methylene chloride/ diethyl ether gave a total of 3.23 g. (52%), m.p. 154°–60° C. The nuclear magnetic resonance and infrared spectra were in agreement with the proposed structure; the material was pure by thin layer chromatography (10% MeOH/CHCl$_3$).

Analysis Calcd. for $C_{34}H_{52}Cl_2N_2O_4$ (MW=623.68): Theory: C, 65.47; H, 8.40; N, 4.49; Found: C, 65.21; H, 8.45; N, 4.47

EXAMPLE 35

5,5-Dimethyl-10-[3-(piperidino)propionyloxy]-8-pentyl-2-(2-propynyl)-1,2,3,4-tetrahydro-5H-[1]benzopyrano-[3,4-d] pryridine tartrate 5,5-Dimethyl-10-hydroxy-8-pentyl-2-(2-propynyl)-1,2,3,4-tetrahydro-5H-[1]benzopyrano[3,4-d]pyridine (1 mm.), dicyclohexylcarbodiimide (1 mm.) and β-piperidinopropionic acid (1 mm.) are combined in 30 ml. of methylene chloride and stirred for 16 hours. The insoluble byproduct of dicyclohexylurea is removed by filtration and the methylene chloride is distilled off using a rotary evaporator. The residue is dissolved in benzene and filtered to remove any insoluble material. The solvent is evaporated and the residue is chromatographed to yield the desired product as neutral material which can be converted to the tartrate by well known methods.

The following compounds are prepared according to the method of Example 10 by reacting the desired benzopyranopyridine with the appropriate acid or acid salt.

EXAMPLE 36

5,5-Dimethyl-8-(3-methyl-2-octyl)-2-(2-propynyl)-1,2,3,4-tetrahydro-10-[4-(thiomorpholino)butyryloxy]-5H-[1]benzopyrano[3,4,-d] pyridine hydrobromide Equimolar amounts of 5,5-dimethyl-10-hydroxy-8-(3-methyl-2-octyl)-2-(2-propynyl)-1,2,3,4,-tetrahydro-5H-[1] benzopyrano[3,4-d]pyridine, γ-thiomorpholinobutyric acid hydrobromide and dicyclohexylcarbodiimide are reacted to form the desired product.

EXAMPLE 37

5,5-Dimethyl-2-benzyl-10-[2-(homopiperidino)acetoxy]-8-hexyl-1,2,3,4,-tetrahydro-5H-[1]benzopyrano[3,4-d]pyridine Equimolar amounts of 5,5-dimethyl-2-benzyl-8-hexyl-10-hydroxy-1,2,3,4-tetrahydro-5H[1]benzopyrano[3,4-d]pyridine, homopiperidinoacetic acid and dicyclohexylcarbodiimide are reacted to form the desired product.

EXAMPLE 38

5,5-Dimethyl-10-[4-morpholino)butyryloxy]-8-(3-methyl-2-octyl)-2-methyl-1,2,3,4-tetrahydro-5H-[1]-benzopyrano[3,4-d] pyridine hydrochloride 5,5-Dimethyl-10-hydroxy-8-(3-methyl-2-octyl)-2-methyl)-1,2,3,4-tetrahydro-5H-[1]benzopyrano[3,4-d]pyridine, γ-morpholinobutyric acid hydrochloride and dicyclohexylcarbodiimide are combined in equimolar amounts in methylene chloride and reacted as in Example 1 to give the desired product.

EXAMPLE 39

2-Benzyl-5,5-dimethyl-10-[4-morpholino)butyryloxy]-8-(3-methyl-2-octyl) 1,2,3,4-tetrahydro-5H-[1]-benzopyrano[3,4-d]pyridine hydrochloride 2-Benzyl-5,5-dimethyl-10-hydroxy-8-(3-methyl-2-octyl) 1,2,3,4-tetrahydro-5H-[1]benzopyrano[3,4-d]pyridine, γ-morpholinobutyric acid hydrochloride and dicyclohexylcarbodiimide are combined in equimolar amounts in methylene chloride and reacted as in Example 1 to give the desired product.

EXAMPLE 40

2-Benzyl-5,5-dimethyl-10-[4-(2-methylpiperidino)-butyryloxy]-8-(1-pentyl)-1,2,3,4-tetrahydro-5H-[1]benzopyrano[3,4-d] pyridine hydrochloride 2-Benzyl-5,5-dimethyl-10-hydroxy-8-(1-pentyl)-1,2,3,4-tetrahydro-5H-[1]benzopyrano[3,4-d]pyridine, γ-(2-methylpiperidino)- butyric acid hydrochloride and dicyclohexylcarbodiimide in equimolar amounts are reacted as in Example 1 to give the desired product.

EXAMPLE 41

5,5-Dimethyl-10-[4-pyrrolidino)butyryloxy]-2-phenethyl-8-(2-tetradecyl)-1,2,3,4-tetrahydro-5H-[1]benzopyrano[3,4-d] pyridine hydrochloride 5,5-Dimethyl-10-hydroxy-2-phenethyl-8-(2-tetradecyl)- 1,2,3,4-tetrahydro-5H-[1]benzopyrano[3,4-d]pyridine, γ-pyrrolidinobutyric acid hydrochloride and dicyclohexylcarbodiimide are reacted in equimolar amounts according to Example 1 to produce the desired product.

EXAMPLE 42

2-Allyl-5,5-diethyl-8-(3-methyl-2-octyl)-10-[4-(piperidino)butyryloxyl]-1,2,3,4-tetrahydro-5H-[1]benzopyrano[3,4-d]- pyridine hydrochloride 2-Allyl-5,5-diethyl-8-(3-methyl-2-octyl)-10-hydroxy-1,2,3,4-tetrahydro-5H-[1]-benzopyrano[3,4-d]-pyridine, γ-piperidinobutyric acid hydrochloride and dicyclohexylcarbodiimide are reacted in equimolar amounts to produce the desired product.

EXAMPLE 43

2-(2-Cyclohexylethyl)-5,5-dimethyl-8-(1-pentyl)-10-[5-(morpholino)valeryloxy]-1,2,3,4-tetrahydro-5H-[1]benzopyrano[3,4-d]pyridine hydrochloride 2-(2-Cyclohexylethyl)-5,5-dimethyl-10-hydroxy-8-(1-pentyl)-1,2,3,4-tetrahydro-5H-[1]benzopyrano[3,4-d]pyridine, δ-piperidinovaleric acid hydrochloride and dicyclohexylcarbodiimide are reacted in equimolar amounts according to Example 1 to form the desired product.

EXAMPLE 44

2-Cinnamyl-8-cyclopropylmethyl-5,5-di(1-propyl)-10-[4-pyrrolidino)butyryloxy]-1,2,3,4-tetrahydro-5H-[1]benzopyrano[3,4-d]pyridine hydrochloride 2-Cinnamyl-8-cyclopropylmethyl-5,5-di-(1-propyl)-10-hydroxy-1,2,3,4-tetrahydro-5H-[1]benzopyrano[3,4-d]pyridine, γ-pyrrolidinobutyric acid hydrochloride and dicyclohexylcarbodiimide are reacted in equimolar amounts according to Example 1 to form the desired product.

EXAMPLE 45

4,4-Dimethyl-9-hydroxy-7-(3-methyl-2-octyl)-1,2,3,4-tetrahydrocyclopenta[c][l]benzopyran a. 4-Oxo-9-hydroxy-7-(3-methyl-2-octyl)-1,2,3,4-tetrahydrocyclopenta[c][l]benzopyran A mixture of 8.5 g. (0.0545 mole) of ethyl cyclopentanone-2-carboxylate (Aldrich Chemical Co.), 11.6 g. (0.05 mole) of 5-(3-methyl-2-octyl)resorcinol, and 5.6 g. (3.5 ml; 0.0365 mole) of phosphorus oxychloride was heated under reflux in 50 ml. of benzene for 5 hours. The mixture turned deep red. The cooled solution was added to an excess sodium carbonate/ice mixture and the mixture was then extracted with ether. The organic layer was washed with water, dried and evaporated to give a solid which crystallized from an ethyl acetate/petroleum ether mixture as colorless crystals, m.p. 151°–154°. Recrystallization from methanol containing a few drops of water gave the desired pyrone as colorless crystals, m.p. 154°–156°. N.m.r. confirmed the assigned structure.

Analysis Calcd. for $C_{21}H_{28}O_3$: C, 76.79; H, 8.48; Found: C, 76.98; H, 8.55 b. 4,4-Dimethyl-9-hydroxy-7-(3-methyl-2-octyl)-1,2,3,4-tetrahydrocyclopenta[c][l]benzopyran A solution of 3.28 g. (0.01 mole) of the above prepared pyran, m.p. 154°–156°, in 30 ml. of benzene was added to a refluxing solution of methyl magnesium iodide, prepared from 2.4 g. (0.1 mole) of magnesium turnings and 14.2 g. (0.1 mole) of iodomethane in 30 ml. of ether. The mixture was refluxed for 16 hours and decomposed with an ice and ammonium chloride mixture. The organic layer was separated and the aqueous layer was extracted with benzene. The combined extracts were washed with water and dried. After evaporation of the solvent, the residue was taken up in n-heptane and boiled with a few drops of hydriodic acid for 20 minutes. A violent reaction occurred. The solution was cooled, treated with decolorizing carbon, and evaporated to a gum. The gum was distilled at 0.05 mm through a short path distillation apparatus to give 1.9 g. of the desired product as an amber colored liquid (pot temperature, 230°). Ultraviolet and n.m.r. analysis confirmed the structure.

Analysis Calcd. for $C_{23}H_{34}O_2$: C, 80.65; H, 10.01; Found: C, 80.59; H, 9.96

EXAMPLE 46

4,4-Dimethyl-7-(3-methyl-2-octyl)-9-]4-(piperidino)-butyryloxy]-1,2,3,4-tetrahydrocyclopenta[c][l]benzopyran hydrochloride 5.0 g. (14.6 mmoles) of 4,4-dimethyl-9-hydroxy-7-(3-methyl-2-octyl)-1,2,3,4-tetrahydrocyclopenta[c][1-]benzopyran, 3.14 g. (15.2 mmoles) of dicyclohexylcarbodiimide and 3.15 g. (15.2 mmoles) of γ-piperidinobutyric acid hydrochloride (m.p. 190°–192°), Cruickshank & Sheehan, J. Am. Chem. Soc. 83, 2891 (1961), were combined with 250 ml. of methylene chloride and stirred for a total of 40 hours at room temperature. The insoluble by-product of dicyclohexylurea was separated by filtration and the methylene chloride was removed using a rotary evaporator. The brown residue was treated with approximately 75 ml. of benzene, and filtered to remove a small amount of insoluble material. The benzene was evaporated and the brown viscous residue was triturated with about 200 ml. of ether to give 4.3 g. of crude product as a light brown solid, m.p. 174°–176°. Recrystallization from benzene gave a total of 3.5 g. (45%) of product as colorless crystals, m.p. 174°–176°. The infrared and nmr spectra are in agreement with the proposed structure.

Analysis Calcd. for $C_{32}H_{50}ClNO_3$. C, 72.21; H, 9.47; N, 2.63; Found: C, 72.20; H, 9.56; N, 2.62

EXAMPLE 47

4,4-Dimethyl-7-(3-methyl-2-octyl)-9-[3-(piperidino)-propionyloxy]-1,2,3,4-tetrahydrocyclopenta[c][1]-benzopyran hydrochloride 2.8 g. (8.2 mmoles) of 4,4-dimethyl-9-hydroxy-7-(3-methyl-2-octyl)-1,2,3,4-tetrahydrocyclopenta[c][1-]benzopyran, 1.77 g. (8.6 mmoles) of dicyclohexylcarbodiimide and 1.65 g. (8.5 mmoles) of β-piperidinopropionic acid hydrochloride (m.p. 216°–220°, J. Am. Chem. Soc. 73, 3168 (1951)) were combined with 125 ml. of methylene chloride and stirred at room temperature for about 20 hours. The reaction mixture was filtered and the methylene chloride removed using a rotary evaporator. The residue was treated with benzene and filtered to remove a small quantity of insoluble material. The benzene was evaporated and the dark viscous residue was chromatographed using 100 g. of 60–100 mesh Florisil activated magnesium silicate and methanol/chloroform graded solvent mixtures. Chromatography gave a small quantity of orange oil which was dissolved in ether and treated with a solution of ethereal HCl. The desired compound appeared as white crystals which were filtered and washed with additional ether. The colorless crystals (86 mg., m.p. 106°–107°) were pure by thin layer chromatography (10% MeOH/CHCl$_3$) and the nmr and infrared spectra are in agreement with the proposed structure.

Analysis Calcd. for $C_{31}H_{48}ClNO_3$: C, 71.85; H, 9.34; N, 2.70; Found: C, 71.72; H, 9.34; N, 2.77

EXAMPLE 48

1-[4-(morpholino)butyryloxy]-3-n-pentyl-6,6,9-trimethyl-10a,6a,7,8-tetrahydrodibenzo[b,d]pyran hydrochloride 0.7 g. (2.23 mmoles) of 1-Hydroxy-3-n-pentyl-6,6,9-trimethyl-10a,6a,7,8-tetrahydrodibenzo[b,d]pyran, 0.48 g. (2.28 mmoles) of γ-morpholinobutyric acid hydrochloride (Cruickshank and Sheehan, J. Am. Chem. Soc. 83, 2891 (1961), m.p. 180°–182°), and 0.48 g. (2.35 mmoles) of dicyclohexylcarbodiimide (Aldrich) were combined with 35 ml. of methylene chloride and stirred at room temperature for a total of 40 hours. The insoluble by-product of dicyclohexylurea was separated by filtration and the methylene chloride was removed using a rotary evaporator. The resulting residue was dissolved in about 20 ml. of benzene and a small amount of insoluble material was removed by filtration. The benzene was evaporated and the residue dried in vacuo to give 0.7 g. of fluffy, white material. Crystallization from benzene/pet ether gave 0.4 g. of product as colorless crystals, m.p. 99°–101°. The material was pure by thin layer chromatography (10% MeOH/CHCl$_3$); the infrared and nmr spectra are in agreement with the proposed structure.

Analysis Calcd. for $C_{29}H_{44}ClNO_4 \cdot 1/2H_2O$: C, 67.60; H, 8.81; N, 2.72; Found C, 67.74; H, 8.68; N, 2.81

EXAMPLE 49

4,4-Dimethyl-7-(3-methyl-2-octyl)-9-[4-(morpholino)butyryloxy]-1,2,3,4-tetrahydrocyclopenta[c][1]benzopyran hydrochloride 6.4 g. (18.7 mmole) of 4,4-Dimethyl-9-hydroxy-7-(3methyl-2-octyl)-1,2,3,4-tetrahydrocyclopenta[c][1-]benzopyran, 4.33 g. (21.0 mmoles) of cyclohexylcarbodiimide and 4.26 g. (20.3 mmoles) of γ-morpholinobutyric acid hydrochloride were combined with 325 ml. of methylene chloride and stirred at room temperature for a total of 24 hours. The insoluble by-product of dicyclohexylurea was separated for filtration and the methylene chloride was removed using a rotary evaporator. The brown viscous residue was dissolved in about 100 ml. of benzene and the benzene solution was filtered to remove a small amount of insoluble material. The benzene was removed using a rotary evaporator and the remaining residue was triturated with approximately 250 ml. of ether. The solid which formed was filtered, washed with ether and dried to give 8.6 of beige solid. The material was crystallized from benzene/ether to give 3.5 g. of product as a colorless solid, m.p. 151°–153°. The material was pure by thin layer chromatography (10% MeOH/CHCl$_3$); the infrared and nmr spectra are in agreement with the proposed structure. An additional 3.3 g. of somewhat impure material was recovered from the mother liquor.

Analysis Calcd. for $C_{31}H_{48}ClNO_4$: C, 69.70; H, 9.06; N, 2.62; Found: C, 69.43; H, 8.98; N, 2.55

EXAMPLE 50

4,4-Dimethyl-9-[4-(morpholino)butyryloxy]-7-n-pentyl-1,2,3,4-tetrahydrocyclopenta[c][1]benzopyran hydrochloride 1.0 g. (3.5 mmoles) of 4,4-dimethyl-9-hydroxy-7-n-pentyl-1,2,3,4-tetrahydrocylopenta[c][1]benzopyran, 0.76 g. (3.63 mmoles) of γ-morpholinobutyric acid hydrochloride and 0.76 g. (3.70 mmoles) of dicyclohexylcarbodiimide were combined in 75 ml. of methylene chloride and stirred at room temperature for 24 hours. The insoluble by-product of dicyclohexylurea was removed by filtration and the methylene chloride sodium was concentrated to 20 ml. Cyclohexane was added until the desired compound was obtained as a colorless solid. Recrystallization from methylene chloride/cyclohexane gave 1.1 g. (65% yield) of product as colorless crystals, m.p. 181°–183°. The material was pure by thin layer chromatography (5% NeOH/CHCl$_3$); the infrared and nmr spectra are consistent with the proposed structure.

Analysis Calcd. for $C_{27}H_{40}ClNO_4$: C, 67.83; H, 8.43; N, 2.93; Found: C, 67.75; H, 8.31; N, 2.90

EXAMPLE 51

3-n-pentyl-1-[4-(piperidino)butyryloxy]-6,6,9-trimethyl-10a,6a,7,8-tetrahydrodibenzo[b,d]pyran hydrochloride 0.46 g. (1.47 mmoles) of 1-Hydroxy-3-n-pentyl-6,6,9-trimethyl-10a,6a,7,8-tetrahydrodibenzo[b,d]pyran, 0.31 g. (1.47 mmoles) of γ-piperidinobutyric acid hydrochloride and 0.32 g. (1.55 mmoles) of dicyclohexylcarbodiimide were combined in 25 ml. of methylene chloride and stirred at room temperature for 4 hours. The insoluble by-product of dicyclohexylurea was removed by filtration and the methylene chloride was evaporated to give a gummy yellowish residue. The gummy material was triturated several times with petroleum ether and dried in vacuo to give 350 mg. of product as a colorless foam-like solid. The sample was pure by thin-layer chromatography (10% MeOH/CHCl$_3$) and the infrared spectrum was consistent with the proposed structure.

EXAMPLE 52

γ-Pyrrolidinobutyric acid hydrochloride 30.0 g. (0.13 mole) of Methyl γ-iodobutyrate (F.F. Blicke, W.B. Wright and M.F. Zienty, *J. Amer. Chem. Soc.* 63, 2488 (1941) was combined with 36 g. of pyrrolidine (Aldrich) in 300 ml. of benzene, heated at 60° for 0.5 hour and stirred at room temperature for 16 hours. A dark orange layer formed. The benzene solution was decanted, concentrated and distilled (b.p. 100° at 15 mm Hg) to give 10 g. of colorless liquid. The infrared and nmr spectra indicated that product to be methyl Γ-pyrrolidinobutyrate. This material was dissolved in 100 ml. of 18% hydrochloric acid and heated at reflux for 28 hours. The solution was concentrated under reduced pressure to give a semi-solid which was triturated with acetone and filtered. Recrystallization from acetic acid/acetone gave 8.3 g. (33%) of the desired acid hydrochloride as colorless crystals, m.p. 126°–127°. The infrared and nmr spectra are consistent with the proposed structure.

Analysis Calcd. for $C_8H_{16}ClNO_2$: C, 49.60; H, 8.33; N, 7.28; Found: C, 49.70; H, 8.14; N, 7.21

EXAMPLE 53

4,4-Dimethyl-7-(3-methyl-2-octyl)-9-[4(pyrrolidino)butyryloxy]-1,2,3,4-tetrahydrocyclopenta[c][1]benzopyran hydrochloride 3.21 g. (9.37 mmole) of 4,4-Dimethyl-9-hydroxy-7-(3-methyl-2-octyl)-1,2,3,4-tetrahydrocyclopenta[c][1]benzopyran was combined with 1.82 g. (9.37 mmole) of γ-pyrrolidinobutyric acid hydrochloride and 2.06 g. (10.0 mmole) of dicyclohexylcarbodiimide in 150 ml. of methylene chloride and stirred at room temperature for 2½ hours. The insoluble by-product of dicyclohexylurea was removed by filtration and the filtrate was evaporated to give a residue which crystallized upon standing. The material was triturated with ether and filtered. Recrystallization from benzene/ether gave 3.5 g. (72%) of product as colorless crystals, m.p. 138°–141°. The material was pure by thin layer chromatography (10% MeOH/CHCl₃); the infrared and nmr spectra are consistent with the proposed structure.

Analysis Calcd. for $C_{31}H_{48}ClNO_4$: C, 71.85; H, 9.34; H, 2.70; Found: C, 71.91; H, 9.18; N, 2.81

EXAMPLE 54

γ-Homopiperidinobutyric acid hydrochloride 23.0 g. (0.1 mmole) of Methyl γ-iodobutyrate (F.F. Blicke, W.B. Wright and M.F. Zienty, *J. Amer. Chem. Soc.* 63, 2488 (1941) was combined with 25.0 g. (0.4 mole) of homopiperidine (Aldrich) and heated at 70° for 3 hours. The precipitate of amine hydroiodide was removed by filtration and the filtrate was concentrated to an orange oil. The methyl γ-homopiperidinobutyrate distilled as 14.0 g. of colorless liquid at 0.5 mm., b.p. 70°–71°. This material was dissolved in 75 ml. of aqueous 18% hydrochloric acid solution and heated at reflux for 16 hours. The solution was concentrated under reduced pressure to give a semi-solid residue which was triturated with acetone and filtered. Recrystallization from acetic acid/acetone gave 10.0 g. (45%) of product as colorless crystals, m.p. 178°–179°. The infrared and nmr spectra are consistent with the proposed structure.

Analysis Calcd. for $C_{10}H_{20}ClNO_2$: C, 54.20; H, 9.09; N, 6.32; Found: C, 54.21; H, 8.93; H6.26

EXAMPLE 55

4,4-Dimethyl-9-[4-(homopiperidino)butyryoxy]-7-(3-methyl-2-octyl)-1,2,3,4-tetrahydrocyclopenta[c][1]benzopyran hydrochloride 4.0 g. (11.7 mmole) of 4,4-Dimethyl-9-hydroxy-7-(3-methyl-2-octyl)-1,2,3,4-tetrahydrocyclopenta[c][1]benzopyran was combined and 2.6 g. (11.7 mmole) of γ-homopiperidinobutyric acid hydrochloride and 2.6 g. (12.5 mmole) of dicyclohexylcarbodiimide in 175 ml. of methylene chloride and stirred at room temperature for 3.5 hours. The dicyclohexylurea was separated by filtration and the methylene chloride was removed on a rotary evaporator. The residue was dissolved in a methylene chloride/cyclohexane mixture and the small amount of solid which appeared was removed by filtration. The solvents were evaporated to give a residue which crystallized from benzene/ether. Recrystallization gave 5.0 g. (78%) of product as colorless crystals, m.p. 150°–152.5°. The sample was pure by thin layer chromatography (10% MeOH/CHCl₃), and the infrared and nmr spectra are consistent with the proposed structure.

Analysis Calcd. for $C_{33}H_{52}ClNO_3$: C, 72.45; H, 9.59; N, 2.56; Found: C, 72.57; H, 9.44; N, 2.58

EXAMPLE 56

γ-Morpholinobutyric acid hydrobromide 15 g. (0.052 mole) of Methyl γ-morpholinobutyrate (Cruickshank and Sheehan, *J. Am. Chem. Soc.* 83, 2891 (1961) was dissolved in a mixture of 45 ml. of 47% hydrobromic acid and 45 ml. of water and heated for 16 hours at reflux. The solution was taken to dryness under reduced pressure, and the solid which formed was triturated with acetone. The material was filtered and crystallized from 60 ml. of acetic acid to give 12.4 g. (95%) of product as colorless crystals, m.p. 151°–152.5°. The infrared and nmr spectra are consistent with the proposed structure.

Analysis Calcd. for $C_8H_{16}BrNO_3$: C, 37,81; H6.36; N, 5.51; Found: C, 37.80; H, 6.28; N, 5.47

EXAMPLE 57

1-[4-(Morpholino)butyryloxy]-3-n-pentyl-6,6,9-trimethyl-10a,6a,7,8-tetrahydrodibenzo[b,d]pyran hydrobromide 3.54 g. (11.27 mmole) of 1-Hydroxy-3-n-pentyl-6,6,9-trimethyl-10a,6a,7,8-tetrahydrodibenzo[b,d]pyran, 2.86 g. (11.27 mmole) of γ-morpholinobutyric acid hydrobromide and 2.50 g. (12.12 mole) of dicyclohexylcarbodiimide were combined in 200 ml. of methylene chloride and stirred at room temperature for 24 hours. The reaction mixture was cooled and the by-product of dicyclohexylurea was removed by filtration. The volume of methylene chloride was reduced and 25 ml. of cyclohexane was added. The mixture was cooled and the small amount of solid which formed was removed by filtration. All solvents were removed on a rotary evaporator and the residue was dried in vacuo. The resulting foamy material was dissolved in a mixture of benzene and ether and placed in cold storage to yield 3.0 g. (50%) of product as colorless crystals, m.p. 103°–105°. The compound gave a $R_f$ 0.5 in 5% MeOH/CHCl₃. The infrared and nmr are consistent with the proposed structure.

Analysis Calcd. for $C_{29}H_{44}BrNO_4 \cdot 1/2H_2O$: C, 62.20; H, 8.10; N, 2.50; Found: C, 62.30; H, 7.95; N, 2.68

EXAMPLE 58

3-(3-Methyl-2-octyl)-1-[4-(morpholino)butyryloxy]-6,6,9-trimethyl-7,8,9,10-tetrahydro-6H-dibenzo[b,d]pyran hydrobromide 4.12 g. (11.15 mmole) of 1-Hydroxy-3-(3-methyl-2-octyl)-6,6,9-trimethyl-7,8,9,10-tetrahydro-6H-dibenzo[b,d]pyran was combined with 2.84 g. (11.15 mmole) of γ-morpholinobutyric acid hydrobromide and 2.48 g. (12.0 mmole) of dicyclohexylcarbodiimide in 250 ml. of methylene chloride and stirred at room temperature for 16 hours. The by-product of dicyclohexylurea was removed by filtration and the filtrate was evaporated to give a golden, viscous residue. The material was dissolved in ether and the solid which appeared was removed by filtration. Recrystallization from benzene/ether gave 2.8 g. (41%) of product as colorless crystals, m.p. 120°–122°. The compound showed an $R_f$ 0.7 in 10 % $MeOH/CHCl_3$; the infrared and nmr spectra are consistent with the proposed structure.

Analysis Calcd. for $C_{33}H_{52}BrNO_4$: C, 65,34; H, 8.64; N, 2.27; Found: C, 65,47; H, 8.63; N, 2.49

EXAMPLE 59

3-(3-Methyl-2-octyl)-1-[4-(piperidino)butyryloxy]-6,6,9-trimethyl-7,8,9,10-tetrahydro-6H-dibenzo[b,d]pyran hydrochloride 2.5 g. (6.76 mmole) of 1-Hydroxy-3-(3-methyl-2-octyl)-6,6,9-trimethyl-7,8,9,10-tetrahydro-6H-dibenzo[b,d]pyran was combined with 1.41 g. (6.76 mmole) of γ-piperidinobutyric acid hydrochloride and 1.48 g. (7.16 mmole) of dicyclohexylcarbodiimide in 125 ml. of methylene chloride and stirred at room temperature for 16 hours. The by-product of dicyclohexylurea was removed by filtration and the filtrate was evaporated to give a light brown residue. The residue was dissolved in ether and the small amount of solid which appeared was removed by filtration. The ether was removed on a rotary evaporator and the gummy residue which remained was triturated several times with small quantities of hexane. The material as thoroughly dried to give 2.8 g. (74%) of product as a colorless powder. The material was pure by thin layer chromatography (10% $MeOH/CHCl_3$); the infrared and nmr spectra are consistent with the desired product.

Analysis Calcd. for $C_{34}H_{54}ClNO_3$: C, 72.89; H, 9.71; N, 2.50; Found: C, 72.36; H, 9.58; N, 2.67

EXAMPLES 60–63

The following compounds are prepared according to the method of Example 46 by reacting the appropriate acid with the corresponding benzopyran and dicyclohexylcarbodiimide:

4,4-Dimethyl-7-(3-methyl-2-octyl)-9-[5-(piperidino)valeryloxy]-1,2,3,4-tetrahydrocyclopenta[c][1]benzopyran from 4,4-dimethyl-9-hydroxy-7-(3-methyl-2-octyl)-1,2,3,4-tetrahydrocyclopenta[c][1]benzopyran and δ-piperidinovaleric acid.

4,4-Dimethyl-7-n-hexyl-9-(morpholinoacetyloxy)-1,2,3,4-tetrahydrocyclopenta[c][1]benzopyran tosylate from 4,4-dimethyl-7-n-hexyl-9-hydroxy-1,2,3,4-tetrahydrocyclopenta[c][1]benzopyran and morpholinoacetic acid tosylate.

9-[4-Azetidino butyryloxy]-4,4,7-trimethyl-1,2,3,4-tetrahydrocyclopenta[c][1benzopyran tartrate from 9-hydroxy-4,4,7-trimethyl-1,2,3,4-tetrahydrocyclopenta[c][1]benzopyran and γ-azetidinobutyric acid tartrate.

4,4-Dimethyl-7-(2-tetradecyl)-9-[8-(thiomorpholino)octanoyloxy]-1,2,3,4-tetrahydrocyclopenta[c][1]benzopyran from 4,4-dimethyl-9-hydroxy-7-(2-tetradecyl)-1,2,3,4-tetrahydrocyclopenta[c][1]benzopyran and thiomorpholinooctanoic acid.

The present invention includes within its scope pharmaceutical compositions comprising, as an active ingredient, at least one of the compounds of this invention in association with a pharmaceutically acceptable carrier or diluent. The compounds of this invention exhibit both oral and parenteral activity and can be formulated in dosage forms for oral, parenteral or rectal administration.

Solid dosage forms for oral administration include capsules, tablets, pills, powders and grandules. In such solid dosage forms, the active compound is admixed with at least one inert diluent such as sucrose, lactose or starch. Such dosage forms can also comprise, as is normal practice, additional substances other than inert diluents, e.g., lubricating agents such as magnesium stearate, and sweetening and flavoring agents. Tablets and pills can additionally be prepared with enteric coatings.

Liquid dosage forms for oral administration include pharmaceutically acceptable emulsions, solutions, suspensions, syrups and elixirs containing inert diluents commonly used in the art, such as water. Besides inert diluents, such compositions can also include adjuvants, such as wetting agents, emulsifying and suspending agents such sweetening, flavoring and perfuming agents.

Preparations according to this invention for parenteral administration include sterile aqueous or nonaqueous solutions, suspensions or emulsions. Examples of non-aqueous solvents or vehicles ar propylene glycol, polyethylene glycol, vegetable oils, such as olive oil, and injectable organic esters such as ethyl oleate. Such dosage forms may also contain adjuvants such as preserving, wetting, emulsifying and dispersing agents. They may be sterilized by, for example, filtration through a bacteria-retaining filter, by incorporating sterilizing agents into the compositions, by irradiating the compositions, or by heating the compositions. They can also be manufactured in the form of sterile solid compositions which can be dissolved in sterile water, or some other sterile injectable medium immediately before use.

Compositions for rectal administration are suppositories which may contain in addition to the active substance, excipients such as cocoa butter or a suppository wax.

The dosage of active ingredients in the compositions of this invention may be varied; however, it is necessary that the amount of the active ingredient shall be such that a suitable dosage form is obtained. The selected dosage depends upon the desired therapeutic effect, on the route of administration and on the treatment. Generally, dosage levels of between 0.01 – 20 mg./kg. of body weight daily are administered to patients in need of analgesis or tranquilization.

The following example further illustrates the pharmaceutical compositions which are a feature of this invention.

EXAMPLE 64

Tablets weighting 200 mg. and having the following compositions are prepared by standard tableting procedures:

| Ingredient | Mg. |
| --- | --- |
| 4,4-Dimethyl-7-(3-methyl-2-octyl)-9-[4-(piperidino)butyryloxy]-1,2,3,4-tetrahydrocyclopenta[c][1]benzopyran hydrochloride | 100 |
| Starch | 90 |
| Colloidal silica | 5 |
| Magnesium stearate | 1 |

It will be understood by those skilled in the art that the above compositions can contain any of the compounds of this invention.

The starting materials can be prepared according to the method described in C. A. 72: 1274 and U.S. Pat. No. 3,639,427.

The following example further illustrate the present invention.

EXAMPLE 65

Preparation of 2-(3,5-dimethoxyphenyl)-5-(4-fluorophenyl)pentane

A solution of 77 g. of 3-(4-fluorophenyl)propylbromide in 300 ml. of ether was added dropwise over a 2 hour period to a refluxing solution of 10 g. of magnesium in 100 ml. of ether. The reaction mixture was refluxed for an additional 30 minutes after the addition was completed. A solution of 68 g. of 3,5-dimethoxyacetophenone in 100 ml. of ether was then added dropwise to the reaction and the reaction mixture was refluxed for 1½ hours. To the reaction was added 300 ml. of a saturated ammonium chloride solution dropwise with stirring. The layers were separated and the aqueous layer extracted with ether. The ether extract was dried over magnesium sulfate and the ether removed in vacuo to give an oil. An additional 111.7 g. of 3(4-fluorophenyl)propylbromide was worked up in the above manner. The products from both runs were hydrogenated in ethanol-HCl using palladium as the catalyst. The solvents and catalyst were removed and the crude material distilled to yield 169.0 g. of 2-(3,5-dimethoxyphenyl)-5-(4-fluorophenyl) pentane, b.p. 145–155/0.05 mmHg.

Analysis Calcd. for $C_{19}H_{23}O_2F$: C, 75.60; H, 7.69 Found: C, 75.87; H, 7.98

EXAMPLE 66

Preparation of 2-(3,5-dihydroxyphenyl)-5-(4-fluorophenyl)pentane

Fifty grams of the above prepared 2-(3,5-dimethoxyphenyl)-5-(4-fluorophenyl)pentane, 450 ml. of acetic acid and 180 ml. of 48% HBr in water were mixed. While cooling, the mixture was saturated with hydrogen bromide gas (approximately ½ hour). The reaction was placed in an 87° bath and stirred for 17 hours. The reaction was then concentrated in vacuo and the residue neutralized with $K_2CO_3$ and $NaHCO_3$, extracted with ether, treated with charcoal and $MgSO_4$ and filtered to yield 45 g. of 2-(3,5-dihydroxyphenyl)-5-(4-fluorophenyl)pentane as a brown oil which distills at 180°/0.01 mmHg.

Analysis Calcd. for $C_{17}H_{25}O_2F$: C, 74.20; H, 6.98; Found: C, 73.56; H, 7.04

EXAMPLE 67

Preparation of 3-(4-fluorophenyl-1-methylbutyl)-1-hydroxy-6,9,9-trimethyl-6a,7,8,10a-tetrahydrodibenzo[b,d]pyran Fourteen grams of the above prepared 2-(3,5-dihydroxyphenyl)-5-(4-fluorophenyl)pentane, 11 g. of ethyl, 4-methyl-2-cyclohexane-1-carboxylate, 60 ml. of benzene and 3.6 ml. of $POCl_3$ were stirred and refluxed for 4 hours and stirred at room temperature for 12 hours. The reaction was poured into water and sodium bicarbonate, extracted with ether, dried over magnesium sulfate and concentrated to an oil. The oil was extracted with pentane to remove the unreacted keto ester.

The oil was then dissolved in 80 ml. of ether and added to a methyl magnesium bromide solution prepared from 13 g. of magnesium and 60 g. of methyl bromide in 350 ml. of a saturated aqueous ammonium chloride solution. The ether layer was separated, concentrated to dryness and dissolved in 300 ml. of benzene. To the benzene solution was added 0.05 g. of ToSOH and the reaction was refluxed for 2 hours, passing the condensing liquid through 4A molecular sieves. The benzene layer was extracted with sodium bicarbonate in water, concentrated to dryness and dissolved in 500 ml. of pentane. Charcoal was added to the pentane solution and the solution was filtered. The reaction was then chromatographed on a Florosil activated aluminum magnesium silicate 42 mm × 30 inch column and eluted with 95% pet ether and 5% ethyl ether to yield 10.4 g. of product as a colorless gum.

Analysis Calcd. for $C_{26}H_{30}O_2F$: C, 79.20; H, 8.18; Found: C, 79.36; H, 8.50

EXAMPLE 68

Preparation of 1-hydroxy-3-(phenyl-1-methylbutyl)-6,9,9-trimethyl-6a,7,8,10a-tetrahydrodibenzo[b,d]pyran 1-Hyroxy-3-(phenyl-1-methylbutyl-6,9,9-trimethyl-6a,7,9,10a-tetrahydrodibenzo[b,d]pyran was prepared according to the method of Example 47 from 2-(3,5-hydroxy-phenyl)-5-phenylpentane.

EXAMPLE 69

Preparation of 7-(4-fluorophenyl-1-methylbutyl)-9-hydroxy-4-oxo-1,2,3,4-tetrahydrocyclopenta[c][1]benzopyrane Twenty-two grams of 5-(1-methyl-4-p-fluorophenyl) butyl resorcinol, 80 ml. of benzene, 6 ml. of $POCl_3$, 1 drop of water and 13.0 g. of 2-carbethoxycyclopentanone were refluxed for 8 hours and then stirred at room temperature for 8 hours. The solution was concentrated in vacuo and the residue taken up in either and neutralized with potassium bicarbonate solution. The organic phase was dried over $MgSO_4$ and concentrated. The residue was crystallized from $CH_3CN$ to yield 15.6 g. (7-4-fluorophenyl-1-methylbutyl)-9-hydroxy-4-oxo-1,2,3,4-tetrahydrocyclopenta[c][1]benzopyran, m.p. 133–135° C.

Analysis Calcd. for $C_{23}H_{23}O_3F$: C, 75.50; H, 6.33; Found: C, 75.15; H, 6.21

EXAMPLE 70

Preparation of
4,4-dimethyl-7-(4-fluorophenyl-1-methylbutyl)-9-hydroxy-1,2,3,4-tetrahydrocyclopenta[c][1]benzopyran A solution of 15 gm. of the above prepared pyrone in 30 ml. of ether and 50 ml. of benzene were added slowly to a solution of $CH_3MgBr$ (0.423 mole) in 250 ml. of ether. The reaction was refluxed for 16 hours, and then 500 ml. of a saturated $NH_4Cl$ solution was added slowly. The ether layer was separated, dried over $MgSO_4$ and concentrated. The residue was dissolved in pet ether, decolorized with charcoal and chromatographed on a Florosil activated aluminum magnesium silicate 31mm × 30 inch column to yield 10.9 g. of product as a pale yellow oil.

Analysis Calcd. for $C_{25}H_{29}O_2F$: C, 78.80; H, 7.70; Found: C, 78.80; H, 7.84

EXAMPLE 71

Preparation of
3-(4-fluorophenyl-1-methylbutyl)-1-[4-(piperidino)-butyryloxy]-6,9,9-trimethyl-6a,7,8,10a-tetrahydrodibenzo[b,d]pyran 3-(4-fluorophenyl-1-methylbutyl)-1-hydroxy-6,9,9-trimethyl-6a,7,9,10a-tetrahydrodibenzo[b,d]pyran, (1.603 g.) prepared according to the method of Example 47 was dissolved in 40 ml. of $CH_2Cl_2$, and combined with 0.850 g. of γ-piperidinobutyric acid hydrochloride [m.p. 190°–192°, Cruickshank & Shechan, J. Am. Chem. Soc. 83, 2891 (1967)] and 0.894 g. of dicyclohexylcarbodiimide. The reaction mixture was stirred for 16 hours at room temperature. The insoluble by-product of dicyclohexylurea was separated by filtration and the solution was concentrated in vacuo to yield 2.289 g. of product as a powder which was soluble in water. Thin layer chromatography showed one spot with traces of the starting pyran.

Analysis Calcd. for $C_{36}H_{48}NO_3F \cdot HCl \cdot 1\frac{1}{2}H_2O$: C, 68.74; H, 8.41; N, 2.58; Cl, 5.76; Found: C, 69.10; H, 8.38; N, 2.24; Cl, 5.67

EXAMPLE 72

4,4-Dimethyl-7-(4-fluorophenyl-1-methylbutyl)-9-[4-(piperidino)butyryloxy]-1,2,3,4-tetrahydrocyclopenta[c][1]benzopyran hydrochloride 5.0 g. (14.6 mmoles) of 4,4-dimethyl-9-hydroxy-7-(4-fluorophenyl-1-methylbutyl)-1,2,3,4-tetrahydrocyclopenta [c][1]benzopyran, prepared according to the method of Example 50, 3.14 g. (15.2 mmoles) of dicyclohexylcarbodiimide and 3.15 g. (15.2 mmoles) of γ-piperidinobtyric acid hydrochloride (m.p. 190°–192°), Cruickshank & Sheehan, J. Am. Chem. Soc. 83, 2891 (1961), are combined with 250 ml. of methylene chloride and stirred for a total of 40 hours at room temperature. The insoluble by-product of dicyclohexylurea is separated by filtration and the methylene chloride is removed using a rotary evaporator. The brown residue is treated with approximately 75 ml. of benzene, and filtered to remove a small amount of insoluble material. The benzene is evaporated and the viscous residue is triturated with about 200 ml. of ether to give the crude product. Recrystallization from benzene yields the desired product.

EXAMPLE 73

4,4-Dimethyl-7-(4-fluorophenyl-1-methylbutyl-9-]3-(piperidino)-propionyloxy]-1,2,3,4-tetrahydrocyclopenta[c][1]benzopyran hydrochloride 2.8 g. (8.2 mmoles) of 4,4-dimethyl-9-hydroxy-7-(4-fluorophenyl-1-methylbutyl)-1,2,3,4-tetrahydrocyclopenta [c][1]benzopyran, prepared according to the method of Example 50, 1.77 g. (8.6 mmoles) of dicyclohexylcarbodiimide and 1.65 g. (8.5 mmoles) of β-piperidinopropionic acid hydrochloride (m.p. 216°–220°, J. Am. Chem. Soc. 73, 3168 (1951)) are combined with 125 combined with 125 ml. of methylene chloride and stirred at room temperature for about 20 hours. The reaction mixture is filtered and the methylene chloride removed using a rotary evaporator. The residue is treated with benzene and filtered to remove a small quantity of insoluble material. The benzene is evaporated and the dark viscous residue is chromatographed using 100 g. of 60–100 mesh Florosil activated magnesium silicate and methanol/chloroform graded solvent mixtures. Chromatography yields an oil which is dissolved in ether and treated with a solution of ethereal HCl. The desired compound appears as crystals which are filtered and washed with additional ether to obtain the desired product.

EXAMPLE 74

1-[4-(morpholino)butyryloxy]-3-(phenyl-1-methylbutyl)-6,6,9-trimethyl-6a,7,8,10a-tetrahydrodibenzo[b,d]pyran hydrochloride 0.7 g. (2.33 mmoles) of 1-Hydroxy-3-(phenyl- 1-methylbutyl)-6,6,9-trimethyl-6a,7,8,10a-tetrahydrodibenzo [b,d]pyran, prepared according to the method of Example 48, 0.48 g. (2.28 mmoles) of γ-morpholinobutyric acid hydrochloride (Cruickshank and Sheehan, J. Am. Chem. Soc. 83, 2891 (1961), m.p. 180°–182°) and 0.48 g. (2.35 mmoles) of dicyclohexylcarbodiimide (Aldrich) are combined with 35 ml. of methylene chloride and stirred at room temperature for a total of 40 hours. The insoluble by-product of dicyclohexylurea is removed using a rotary evaporator. The resulting residue is dissolved in about 20 ml. of benzene and a small amount of insoluble material is removed by filtration. The benzene is evaporated and the residue dried in vacuo to give 0.7 g. of material. Crystallization from benzene/pet ether yields the crystalline product.

EXAMPLE 75

4,4-Dimethyl-7-(4-fluorophenyl-1-methylbutyl)-9-[4-(morpholino)-butyryloxy]-1,2,3,4-tetrahydrocyclopenta [c][1]benzopyran hydrochloride 6.4 g. (18.7 mmole) of 4,4-Dimethyl-9-hydroxy-7-(4-fluorophenyl-1-methylbutyl-1,2,3,4-tetrahydrocyclopenta [c][1]benzopyran, prepared according to the method of Example 50, 4.33 g. (21.0 mmoles) of dicyclohexylcarbodiimide and 4.26 g. (20.3 mmoles) of γ-morpholinobutyric acid hydrochloride are combined with 235 ml. of methylene chloride and stirred at room temperature for a total of 24 hours. The insoluble by-product of cicyclohexylurea is separated by filtration and the methylene chloride is removed using a rotary evaporator. The viscous residue is dissolved in about 100 ml. of benzene solution is filtered to remove a small amount of insoluble material. The benzene is removed using a rotary evaporator and the remaining residue is triturated with approximately 250 ml. of ether. The solid which forms is filtered, washed with ether and dried to yield a solid. The material is crystalized from benzene/ether to give the solid product.

EXAMPLE 76

4,4-Dimethyl-9-[4-(morpholino)butyryloxy]-7-(phenyl-1-methylbutyl)-1,2,3,4-tetrahydrocyclopenta[c][1]benzopyran hydrochloride 1.0 g. (3.5 mmoles) of 4,4-dimethyl-9-hydroxy-7-(phenyl-1-methylbutyl)-1,2,3,4-tetrahydrocyclopenta[c][1]benzopyran, 0.76 g. (3.63 mmoles) of γ-morpholinobutyric acid hydrochloride and 0.76 g. (3.70 mmoles) of dicyclohexylcarbodiimide are combined in 75 ml. of methylene chloride and stirred at room temperature for 24 hours. The insoluble by-product of dicyclohexylurea is removed by filtration and the methylene chloride solution is concentrated to 20 ml. Cyclohexane is added until the desired compound is obtained as a colorless solid. Recrystallization from methylene chloride/cyclohexane gives the desired crystalline.

EXAMPLE 77

3-(4-Fluorophenyl-1-methylbutyl)-1-[4-(piperidino)butyryloxy]-6,6,9-trimethyl-6a,7,8,10a-tetrahydrodibenzo[b,d]pyran hydrochloride 0.46 g. (1.47 mmoles) of 3-(4-fluorophenyl)-1-hydroxy-6,6,9-trimethyl-6a,7,8,10a-tetrahydrodibenzo[b,d]pyran, 0.31 g. (1.47 mmoles) of γ-piperidinobutyric acid hydrochloride and 0.32 g. (1.55 mmoles) of dicyclohexylcarbodiimide are combined in 25 ml. of methylene chloride and stirred at room temperature for 4 hours. The insoluble by-product of dicyclohexylurea is removed by filtration and the methylene chloride is evaporated to give a gummy, yellowish residue. The gummy material is triturated several times with petroleum ether and dried in vacuo to give the product as a colorless foam-like solid.

EXAMPLE 78

γ-pyrrolidinobutyric acid hydrochloride 30.0 g. (0.13 mole) of Methyl γ-iodobutyrate (F.F. Blicke, W. B. Wright and M. F. Zienty, *J. Amer. Chem. Soc.* 63, 2488 (1941) was combined with 36 g. of pyrrolidine (Aldrich) in 300 ml. of benzene, heated at 60° for 0.5 hours and stirred at room temperature for 16 hours. A dark orange layer formed. The benzene solution was decanted, concentrated and distilled (b.p. 100° at 15 mm Hg) to give 10 g. of colorless liquid. The infrared and nmr spectra indicated the product to be methyl γ-pyrrolidinobutyrate. This material was dissolved in 100 ml. of 18% hydrochloric acid and heated at reflux for 28 hours. The solution was concentrated under reduced pressure to give a semi-solid which was triturated with acetone and filtered. Recrystallization from acetic acid/acetone gave 8.3 g. (33%) of the desired acid hydrochloride as colorless crystals, m.p. 126°–127°. The infrared and nmr spectra are consistent with the proposed structure.

Analysis Calcd. for $C_8H_{16}ClNO_2$: C, 49.60; H, 8.33; N, 7.28; Found: C, 49.79; H, 8.14; N, 7.21

EXAMPLE 79

4,4-Dimethyl-7-(4-fluorophenyl-1-methylbutyl)-9-[4-(pyrrolidino)butyryloxy]-1,2,3,4-tetrahydrocyclopenta[c][1]benzopyran hydrochloride 3.21 g. (9.37 mmole) of 4,4-Dimethyl-9-hydroxy-7-(4-fluorophenyl-1-methyloctyl)-1,2,3,4-tetrahydrocyclopenta [c][1]benzopyran are combined with 1.82 g. (9.37 mmole) of γ-pyrrolidinobutyric acid hydrochloride and 2.06 g. (10.0 mmole) of dicyclohexylcarbodiimide in 150 ml. of methylene chloride and stirred at room temperature for 2½ hours. The insoluble by-product of dicyclohexylurea is removed by filtration and the filtrate is evaporated to give a residue which crystallized upon standing. The material is triturated with ether and filtered. Recrystallization from benzene/ether gives the product as colorless crystals.

EXAMPLE 80

γ-Homopiperidinobutyric acid hydrochloride 23.0 g. (0.1 mmole) of Methyl-γ-iodobutyrate (F.F. Blicke, W. B. Wright and M. F. Zienty, *J. Amer. Chem. Soc.*, 63, 2488 (1941) was combined with 25.0 g. (0.4 mole) of homopiperidine (Aldrich) and heated at 70° for 3 hours. The precipitate of amine hydroiodide was removed by filtration and the filtrate was concentrated to an orange oil. The methyl γ-homopiperidinobutyrate distilled as 14.0 g. of colorless liquid at 0.5 mm., b.p. 70°–71°. This material was dissolved in 75 ml. of aqueous 18% hydrochloric acid solution and heated at reflux for 16 hours. The solution was concentrated under reduced pressure to give a semisolid residue which was triturated with acetone and filtered. Recrystallization from acetic acid/acetone gave 10.0 g. (45%) of product as colorless crystals, m.p. 178°–179°. The infrared and nmr spectra are consistent with the proposed structure.

Analysis Calcd. For $C_{10}H_{20}ClNO_2$: C, 54.20; H, 9.09; N, 6.32; Found: C, 54.21; H, 8.93; N, 6.26

EXAMPLE 81

4,4-Dimethyl-9-[4-(homopiperidino)butyryloxy]7-(phenyl-1-methylbutyl)-1,2,3,4-tetrahydrocyclopenta[c][1]benzopyrano hydrochloride 4.0 g. (11.7 mmole) of 4,4-Dimethyl-9-hydroxy-7-(phenyl-1-methylbutyl)-1,2,3,4-tetrahydrocyclopenta[c][1]benzopyran is combined with 2.6 g. (11.7 mmole) of γ-homopiperidinobutyric acid hydrochloride and 2.6 g. (12.5 mmole) of dicyclohexylcarbodiimide in 175 ml. of methylene chloride and stirred at room temperature for 3.5 hours. The dicyclohexylurea is separated by filtration and the methylene chloride is removed on a rotary evaporator. The residue is dissolved in a methylene chloride/cyclohexane mixture and the small amount of solid which appears is removed by filtration. The solvents are evaporated to give a residue which crystallizes from benzene/ether. Recrystallization gives the product as colorless crystals.

EXAMPLE 82

γ-Morpholinobutyric acid hydrobromide 15 g. (0.052 mole) of Methyl γ-morpholinobutyrate (Cruickshank and Sheehan, *J. Am. Chem. Soc.* 83, 2891 (1961) was dissolved in a mixture of 45 ml. of 47% hydrobromic acid and 45 ml. of water and heated for 16 hours at reflux. The solution was taken to dryness under reduced pressure, and the solid which formed was triturated with acetone. The material was filtered and crystallized from 60 ml. of acetic acid to give 12.4 g. (95%) of product as colorless crystals, m.p. 151°–152.5°. The infrared and nmr spectra are consistent with the proposed structure.

Analysis Calcd. for $C_8H_{16}BrNO_3$: C, 37.81; H, 6.36; N, 5.51; Found: C, 37.80; H, 6.28; N, 5.347

EXAMPLE 83

1-[4-(Morpholino)butyryloxy]-3-(4-fluorophenyl-1-methylbutyl)-trimethyl-6a,7,8,10a-tetrahydrodibenzo [/b,d]pyran hydrobromide 3.54 g. (11.27 mmole) of 1-Hydroxy-3-(4-fluorophenyl-1-methylbutyl)-trimethyl-6a,7,8,10a-tetrahydrodibenzo[b,d] pyran, 2.86 g. (11.27 mmole) of γ-morpholinobutyric acid hydrobromide and 2.50 g. (12.12 mole) of dicyclohexylcarbodiimide are combined in 200 ml. of methylene chloride and stirred at room temperature for 24 hours. The reaction mixture is cooled and the by-product of dicyclohexylurea is removed by filtration. The volume of methylene chloride is removed by filtration. The volume of methylene chloride is reduced and 25 ml. of cyclohexane is added. The mixture is cooled and the small amount of solid which forms is removed by filtration. All solvents are removed on a rotary evaporator and the residue is dried in vacuo. The resulting material is dissolved in a mixture of benzene and ether and placed in cold storage to yield the crystalline product.

Analysis Calcd. for $C_{29}H_{44}BrNO_4 \cdot 1/2H_2O$: C, 62.20; H, 8.10 N, 2.50; Found: C, 62.30; H, 7.95; N, 2.68

EXAMPLE 84

3-(4-fluorophenyl-1-methylbutyl)-1-[4-(morpholino) butyryloxy]-6,6,9-trimethyl-7,8,9,10-tetrahydro-6H-dibenzo[b,d]pyran hydrobromide 4.12 g. (11.15 mmole) of 1-Hydroxy-3-(4-fluorophenyl)-1-methylbutyl)-6,6,9-trimethyl-7,8,9,10-6H-dibenzo [b,d]pyran are combined with 2.84 g. (11.15 mmole) of γ-morpholinobutyric acid hydrobromide and 2.48 g. (12.0 mmole) of dicyclohexylcarbodiimide in 250 ml. of methylene chloride and stirred at room temperature for 16 hours. The by-product of dicyclohexylurea is removed by filtration and the filtrate is evaporated to give a golden, viscous residue. The material is dissolved in ether and the solid which appears is removed by filtration. Recrystallization from benzene/ether gives the product as colorless crystals.

EXAMPLE 85

3-(4-Fluorophenyl-methylbutyl)-1-[4-(piperidino)-butyryloxy] 6,6,9-trimethyl-7,8,9,10-tetrahydro-6H-dibenzo[b,d]-pyran hydrochloride 2.5 g. (6.76 mmole) of 3-(4-fluorophenyl-1-methylbutyl)-1-hydroxy-6,6,9-trimethyl-7,8,9,10-tetrahydro-6H-dibenzo[b,d]pyran is combined with 1.41 g. (6.76 mmole) of γ-piperidinobutyric acid hydrochloride and 1.48 g. (7.16 mmole) of dicyclohexylcarbodiimide in 125 ml. of methylene chloride and stirred at room temperature for 16 hours. The by-product of dicyclohexylurea is removed by filtration and the filtrate is evaporated to a residue. The residue is dissolved in ether and the small amount of solid which appears is removed by filtration. The ether is removed on a rotary evaporator and the gummy residue which remains is triturated several times with small quantities of hexane. The material is thoroughly dried to yield the product as a powder.

EXAMPLE 86–89

The following compounds are prepared according to the method of Example 50 by reacting the appropriate acid with the corresponding benzopyran and dicyclohexylcarbodiimide:

4,4-Dimethyl-7-(4-fluorophenyl-1-methylbutyl)-9-[5-(piperidino)valeryloxy]-1,2,3,4-tetrahydrocyclopenta[c][1] benzopyran from 4,4-dimethyl-9-hydroxy-7-(4-fluorophenyl-1-methylbutyl)-1,2,3,4-tetrahydrocyclopenta[c][1]benzopyran and δ-piperidinovaleric acid.

4,4-Dimethyl-7-(3-chlorophenyl-n-propyl)-9-(morpholinoacetyloxy)-1,2,3,4-tetrahydrocyclopenta[c][1-]benzopyran tosylate from 4,4-dimethyl-7-(3-chlorophenyl-n-propyl)-9-hydroxy-1,2,3,4-tetrahydrocyclopenta[c][1]benzopyran and morpholinoacetic acid tosylate.

9-[4-Azetidino butyryloxy]-4,4-dimethyl-7-(3,5-difluorophenyl-n-pentyl)tetrahydrocyclopenta[c][1-]benzopyran tartrate from 4,4-dimethyl-7-(3,5-difluorophenyl-n-pentyl)9-hydroxy-1,2,3,4-tetrahydrocyclopenta[c][1]benxopyran and γ-azetidinobutyric acid tartrate.

4,4-Dimethyl-7-(4-fluorophenyl-1-methylbutyl)-9-[8-(thiomorpholino)-octanoyloxy]-1,2,3,4-tetrahydrocyclopenta [c][1]benzopyran from 4,4-dimethyl-9-hydroxy-7-(4-fluorophenyl-1-methylbutyl)-1,2,3,4-tetrahydrocyclopenta[c][1] benzopyran and thiomorpholinooctanoic acid.

EXAMPLE 90

1,2-Dihydro-9-hydroxy-7-(3-methyl-2-octyl)-4-oxo-4H-thieno[2,3-c][1]benzopyran

A. Methyl 3-oxo-2,3,4,5-tetrahydrothiophene-2-carboxylate

The procedure of Woodward and Eastman (J. Am. Chem. Soc. 68, 2229 (1946) was followed for the cyclization of 100 g. (0.55 mole) of methyl 3-(methoxycarbonylmethylthio)propionate to give 56 g. (65%) of methyl 3-oxo-2,3,4,5-tetrahydrothiopene-2-carboxylate.

B. 1,2-Dihydro-9-hydroxy-7-(3-methyl-2-octyl)-4-oxo-4H-thieno [2,3-c][1]benzopyran A solution of 2.5 g. (0.011 mole) of 5-(3-methyl-2-octyl)resorcinol and 2.0 g. (0.013 mole) of the methyl 3-oxo-2,3,4,5-tetrahydrothiopene-2-carboxylate in 50 ml. of absolute ethanol in a three-necked flask equipped with drying tube was cooled in an ice-waer bath and saturated with dry hydrogen chloride. The 5-(3-methyl-2-octyl)resorcinol was prepared according to the method of Adams, MacKenzie and Loewe (J. Am. Chem. Soc. 70, 664–8 (1948). The reaction mixture was allowed to stand for three days at room temperature, during which time a heavy yellow solid formed. The hydrogen chloride was evaporated, the mixture was concentrated and the solid was filtered and washed with ethanol. The yield of the crude benzopyrone thus obtained was 2.6 g. (59%), m.p. 190–205°.

Repeated crystallization from absolute ethanol gave an analytical sample of the material, m.p. 209°–212°.

Anal. Calcd. for $C_{20}H_{26}O_3S$: C, 69.36; H, 7.51; S, 9.25; Found: C, 69.15; H, 7.41; S, 9.30

EXAMPLE 91

1,2-Dihydro-9-hydroxy-7-methyl-4-oxo-4H-thieno[2,3-c][1]benzopyran

Following the procedure similar to that described in Example 1B hereinabove, methyl 3-oxo-2,3,4,5-tetrahydrothiophene-2-carboxylate is reacted with 5-methylresorcinol to give 1,2-dihydro-9-hydroxy-7-methyl-4-oxo-4H-thieno[2,3-c][1]benzopyran.

EXAMPLE 92

1,2-Dihydro-7-(2-heptyl)-9-hydroxyl-4-oxo-4H-thieno[2,3-c][1]benzopyran

Following a procedure similar to that described in Example 1B hereinabove, methyl 3-oxo-2,3,4,5-tetrahydrothiophene-2-carboxylate is reacted with 5-(2-heptyl)resorcinol to give 1,2-dihydro-7-(2-heptyl)-9-hydroxy-4-oxo-4H-thieno [2,3-c][1]benzopyran.

EXAMPLE 93

7-(3-Cyclopropyl-2-propyl)-1,2-dihydro-9-hydroxy-4-oxo-4H-thieno[2,3-c][1]benzopyran Following a procedure similar to that described in Example 1B hereinabove, methyl 3-oxo-2,3,4,5-tetrahydrothiophene-2-carboxylate is reacted with 5-(3-cyclopropyl-2-propyl)resorcinol to give 7-(3-cyclopropyl-2-propyl)-1,2-dihydro-9-hydroxy-4-oxo-4H-thieno[2,3-][1]benzopyran.

EXAMPLE 94

1,2-Dihydro-9-hydroxy-4-oxo-7-(1-pentyl)-4H-thieno[2,3-c][1]benzopyran

Following a procedure similar to that described in Example 1B hereinabove, methyl 3-oxo-2,3,4,5-tetrahydrothiophene-2-carboxylate is reacted with 5-(1-pentyl)resorcinol to give 1,2-dihydro-9-hydroxy-4-oxo-7-(1-pentyl)-4H-thieno[2,3-c][1]benzopyran.

EXAMPLE 95

7-(1-Cyclohexylethyl)-1,2-dihydro-9-hydroxy-4-oxo-4H-thieno[2,3-c][1]benzopyran Following a procedure similar to that described in Example 1B hereinabove, methyl 3-oxo-2,3,4,5-tetrahydrothiophene-2-carboxylate is reacted with 5-(1-cyclohexylethyl) resorcinol to give 7-(1-cyclohexylethyl)-1,2-dihydro-9-hydroxy-4-oxo-4H-thieno[2,3-c][1]benzopyran.

EXAMPLE 96

1,2-Dihydro-7-(2-eicosyl)-9-hydroxy-4-oxo-4-4Hthieno[2,3-c][1]benzopyran

Following a procedure similar to that described in Example 1B hereinabove, methyl 3-oxo-2,3,4,5-tetrahydrothiophene-2-carboxylate is reacted with 5-(2-eicosyl)resorcinol to give 1,2-dihydro-7-(2-eicosyl)-9-hydroxy-4-oxo-4H-thieno [2,3-c[1]-benzopyran.

EXAMPLE 97

1,2-Dihydro-4,4-dimethyl-9-hydroxy-7-(3-methyl-2-octyl)-4H-thieno[2,3-c][1]benzopyran The Grignard reagent was prepared by bubbling bromomethane into a mixture of 7.2 g. (0.3 mole) of magnesium turnings in ether. When all the magnesium had reacted, the solution was refluxed for a short time to remove the excess bromomomethane. A solution of 9.0 g. (0.026 mole) of 1,2-dihydro-9-hydroxy-7-(3-methyl-2-octyl)-4-oxo-4H-thieno[2,3-c][1]benzopyran in 250 ml. of benzene was added to the methylmagnesium bromide and the reaction mixture was kept at 45° for 24 hours. After the addition of saturated ammonium chloride, for benzene/ether layer was separated, and the aqueous layer was extracted with ether. The combined organic layers were washed with water, dried over sodium sulfate and evaporated to give a greenish, gummy residue. The material was pure by tlc (MeOH/CHCl$_3$) and the IR and nmr indicate the compound to be 5-(3-methyl-2-octyl)-2-[4,5-dihydro-2-(2-hydroxy-2-propyl)-3-yl]resorcinol.

2.0 g. of the triol was dissolved in benzene and refluxed for 3 hours in the presence of a small amount of p-toluenesulfonic acid. The benzene solution was concentrated and the residue was chromatographed using Florisil and graded ether/petroleum ether. The infrared, ultraviolet and nmr spectra confirmed the structure.

Anal. Calcd. for C$_{22}$H$_{32}$O$_2$S: C, 73.33; H, 8.91; S, 8.91; Found: C, 73.10; H, 9.16; S, 8.75

The gum exhibitedλEtOH/max 320 mμ (logξ3.951). Infrared, ultraviolet and nmr spectra confirmed the pyran structure.

EXAMPLE 98

1,2-Dihydro-4,4-dimethyl-9-[4-(morpholino)-butyryloxy]-7-(3-methyl-2-octyl)-4H-thieno[2,3-c][1]benzopyran hydrochloride 1.14 g. (3.17 moles) of 1,2-dihydro-4,4-dimethyl-9-hydroxy-7-(3-methyl-2-octyl-4H-thieno[2,3-c][1]benzopyran (prepared according to the method of Example 8) 0.69 g. (3.35 mmoles) of dicyclohexylcarbodiimide and 0.665 g. (3.17 mmoles) of γ-morpholinobutyric acid hydrochloride (Cruickshank and Sheehan J. Am. Chem. Soc., 83, 2891 (1961) m.p. 180°-182°) were combined in 55 ml. of methylene chloride and stirred at room temperature for 4-1/2 hours. The insoluble dicyclohexylurea was removed by filtration and the methylene chloride was removed on a rotary evaporator. The residue crystallized from 30 ml. ether; the solid was filtered and recrystallized from benzene/ether to give 0.5 g. (29%) colorless crystals, m.p. 123°-124°.

The material showed a R$_f$ 0.5 in the tlc (5% MeOH/CHCl$_3$); the IR and nmr spectra are in agreement with the proposed structure.

Anal. Calcd. for C$_{30}$H$_{46}$ClNO$_4$S: C, 65.27; H, 8.40; N, 2.54; Found: C, 64.46; H, 8.19; N, 2.56

EXAMPLE 99

1,2-Dihydro-4,4-dimethyl-9-[4-(piperidino)butyryloxy]-7-(3-methyl-2-octyl)-4H-thieno[2,3-c][1]benzopyran hydrochloride 2.86 g. (7.95 mmoles) of 1,2-dihydro-4,4-dimethyl-9-hydroxy-7-(3-methyl-2-octyl)-4H-thieno[2,3-c][1]benzopyran, 1.65 g. (7.95 mmoles) of γ-piperidinobutyric acid hydrochloride (Cruickshank and Sheehan, J. Am. Chem. Soc. 83, 2891 (1961), m.p. 190°-192°) and 1.72 g. (8.35 mmoles) of dicyclohexylcarbodiimide were combined in 150 ml. of methylene chloride and stirred at room temperature for 4 hours. The insoluble by-product of dicyclohexylurea was removed by filtration and the methylene chloride was removed on a rotary evaporator. The residue was dissolved in benzene (30 ml.) and ethyl ether (30 ml.) and added until a colorless solid appeared. The material was filtered and recrystallized from benzene/ether to give 3.2 g. (73%) of colorless crystals, m.p. 165°–167°.

The material was pure by tlc (10% MeOH/CHCl$_3$); the infrared and nmr spectra are in agreement with the proposed structure.

Anal. Calcd. for C$_{31}$H$_{48}$ClNO$_3$S: C, 67.66; H, 8.79; N, 2.55; Found: C, 67.67; H, 8.88; N, 2.65

EXAMPLE 100

1,2-Dihydro-9-[3-(piperidino)propionoxy]-4,4,7-trimethyl-4H-thieno[2,3-c][1]benzopyran Following the procedure similar to that described in Example 8 hereinabove, 1,2-dihydro-9-hydroxy-7-methyl-4-oxo-4H-thieno[2,3-c][1]benzopyran is reacted with methyl magnesium bromide to give 1,2-dihydro-9-hydroxy-4,4,7-trimethyl-4H-thieno-[2,3-c][1]benzopyran. The benzopyran is then reacted with β-piperidinopropionic acid and dicyclohexylcarbodiimide to yield the desired ester.

EXAMPLE 101

1,2-Dihydro-4,4-dimethyl-7-(2-heptyl)-9-morpholinoacetoxy-4H-thieno[2,3-c][1]benzopyran By reacting 1,2-dihydro-7-(2-heptyl)-9-hydroxy-4-oxo-4H-thieno[2,3-c][1]benzopyran with methyl magnesium bromide in a procedure similar to that described hereinabove in Example 8, there is obtained 1,2-dihydro-4,4-dimethyl-7-(2-heptyl)-9-hydroxy-4H-thieno[2,3-c][1]benzopyran. The benzopyran is then reacted with morpholinoacetic acid and dicyclohexylcarbodiimide to yield the desired ester.

EXAMPLE 102

7-(3-Cyclopropyl-2-propyl)-4,4-dimethyl-1,2-dihydro-9-[4-(piperidino)butyryloxy]-4H-thieno[2,3-c][1]benzopyran hydrochloride 7-(3-cyclopropyl-2-propyl)-1,2-dihydro-9-hydroxy-4-oxo-4H-thieno[2,3-c][1]benzopyran is reacted with methyl magnesium bromide in a procedure similar to that described hereinabove in Example 8 to give 7-(3-cyclopropyl-2-propyl)-4,4-dimethyl, 1,2-dihydro-9-hydroxy-4H-thieno[2,3-c][1]benzopyran which is then reacted with γ-piperidinobutyric acid hydrochloride and dicyclohexylcarbodiimide according to the method of Example 10 to yield the desired ester.

EXAMPLE 103

1,2-Dihydro-4,4-dimethyl-9-[5-(N-methylpiperzino)-valeryloxy]-7-(1-pentyl)-4H-thieno[2,3-c][1]benzopyran dihydrobromide 1,2-Dihydro-9-hydroxy-4-oxo-7-(1-pentyl)-4H-thieno[2,3-c][1]benzopyran is reacted with methyl magnesium bromide in a procedure similar to that described hereinabove in Example 8 to give 1,2-dihydro-4,4-dimethyl-9-hydroxy-7-(1-pentyl)-4H-thieno[2,3-c][1]benzopyran. The benzopyran is then reacted with N-methylpiperazinovaleric acid dihydrobromide and dicyclohexylcarbodiimide according to the method of Example 9 to yield the desired ester.

EXAMPLE 104

7-(1-Cyclohexylethyl)-1,2-dihydro-4,4-dimethyl-9-[3-(homopiperidino)propionyloxy]-4H-thieno[2,3-c][1]benzopyran 7-(1-Cyclohexylethyl)-1,2-dihydro-9-hydroxy-4-oxo-4H-thieno[2,3-c][1]benzopyran is reacted with methyl magnesium bromide according to the procedure described hereinabove in Example 8 to give 7-(1-cyclohexylethyl)-1,2-dihydro-4,4-dimethyl-9-hydroxy-4H-thieno[2,3-c][1]benzopyran. The benzopyran is then reacted with β-homopiperidinopropionic acid and dicyclohexylcarbodiimide according to the method of Example 9 to yield the desired ester.

EXAMPLE 105

1,2-Dihydro-4,4-dimethyl-7-(2-eicosyl)-9-[4-(thiomorpholine)-butyryloxy]-4H-thieno[2,3-c][1]benzopyran 1,2-Dihydro-7-(2-eicosyl)-9-hydroxy-4-oxo-4H-thieno[2,3-c][1]benzopyran is reacted with methyl magnesium bromide according to the procedure described hereinabove in Example 8 to give 1,2-dihydro-4,4-dimethyl-7-(2-eicosyl)-9-hydroxy-4H-thieno[2,3-c][1]benzopyran. The benzopyran is then reacted with γ-thiomorpholinobutyric acid, acetate salt and dicyclohexylcarbodiimide according to the method of Example 10 to yield the desired ester.

EXAMPLE 106

4,4-di(1-hexyl)-1,2-dihydro-9-[4-(pyrrolidino)-butyryloxy]-4H-thieno[2,3-c][1]benzopyran hydrobromide By reacting 1,2-dihydro-9-hydroxy-7-methyl-4-oxo-4H-thieno[2,3-c][1]benzopyran with n-hexyl magnesium bromide, using the procedure described in Example 8, there is obtained 4,4-di(1-hexyl)-1,2-dihydro-9-hydroxy-7-methyl-4H-thieno[2,3-c][1]benzopyran. The benzopyran is then reacted with γ-pyrrolidinobutyric acid, hydrobromide salt and dicyclohexylcarbodiimide according to the method of Example 10 to yield the desired ester.

EXAMPLE 107

7-(3-cyclopropyl-2-propyl)-4,4-di(1-hexyl)-1,2-dihydro-9-morpholinoacetoxy-4H-thieno[2,3-c][1]benzopyran By reacting 7-(3-cyclopropyl-2-propyl)-1,2-dihydro9-hydroxy-4-oxo-4H-thieno[2,3-c][1]benzopyran with n-hexyl magnesium bromide, using the procedure described above in Example 8, there is obtained 7-(3-cyclopropyl-2-propyl)-4,4-di(1-hexyl)-1,2-dihydro-9-hydroxy-4H-thieno[2,3-c][1]benzopyran. The benzopyran is then reacted with morpholinoacetic acid and dicyclohexylcarbodiimide according to the method of Example 9 to yield the desired ester.

EXAMPLE 108

A. Methyl 4-oxo-2,3,4,5-tetrahydrothiopene-3-carboxylate

The procedure of Woodward and Eastman (*J. Am. Chem. Soc.* 68, 2229 (1946) was followed for the cyclization of 48 g. (0.25 mole) of methyl 3-(methoxycarbonylmethylthio)propionate to give 19.8 g. (50%) methyl 4-oxo-2,3,4,5-tetrahydrothiophene-3-carboxylate. The IR and nmr indicate the product to be the desired isomer.

b. 1,3-Dihydro-9-hydroxy-7-(3-methyl-2-octyl)-4-oxo-4H-thieno[3,4-c][1]benzopyran A solution of 20 g. (0.125 mole) of methyl-4-oxo-2,3,4,5-tetrahydrothiophene-3-carboxylate and 32 g. (0.135 mole) of 5-(3-methyl-2-octyl)resorcinol in 200 ml. of absolute ethanol was cooled in an ice-salt bath and saturated with anhydrous hydrogen chloride. The reaction mixture was allowed to stand at room temperature for 72 hours and the solid which formed was removed by filtration. Recrystallization from ethanol gave 16 g. (37%) m.p. 165°–166°. The structure was confirmed by the IR and nmr spectra.

C. 1,3-Dihydro-4,4-dimethyl-7-(3-methyl-2-octyl)-[4-morpholinobutyryloxy]-4H-thieno[3,4,-c][1]benzopyran hydrochloride A suspension of 6.0 g. (0.017 mole) of the above pyrone in 150 ml. of benzene was added to a Grignard reagent prepared by adding bromomethane to 8.47 g. (0.36 mole) of magnesium turnings in 1000 ml. of ether. The mixture was heated at 45° for 24 hours and then decomposed by the addition of dilute hydrochloric acid solution. The organic layer was separated, washed with water, dried over sodium sulfate and evaporated to give a gummy residue. This material was dissolved in benzene and refluxed for 3 hours with a few crystals of p-toluenesulfonic acid. The benzene solution was washed, dried and evaporated to give a dark gum which was chromatographed using Florisil (60–100 mesh) and graded ether/pet ether solvent mixtures. 2.6 g. (42%) of colorless gum was obtained. The material was pure by tlc (20% ether/petroleum ether) and exhibited $\lambda$EtOH/max 284 m$\mu$ (log$\epsilon$4.157). The IR and nmr spectra are in agreement with the proposed structure.

Anal. Calcd. for $C_{22}H_{32}O_2S$: C, 73.33; H, 8.91; Found: C, 73.21; H, 8.76

The benzopyran is reacted with equimolar amounts of $\gamma$-morpholinobutyric acid hydrochloride and dicyclohexylcarbodiimide to obtain the desired product.

EXAMPLE 109

1,2-Dihydro-10-hydroxy-8-(3-methyl-2-octyl)-5-oxo-4H,5H-thiopyrano[3,4-c][1]benzopyran A solution of 6.4 g. (0.027 mole) of 5-(3-methyl-2-octyl-resorcinol of Example 1 and 5.0 g. (0.0266 mole) of ethyl 4-oxo-2,3,4,5,6-tetrahydro-4H-thiopyran-3-carboxylate[prepared according to the method of Bennett and Scorah, J. Chem. Soc., 194 (1972)] in 35 ml. of absolute ethanol was cooled in an ice bath while it was saturated with hydrogen chloride. The resulting deep red solution was tightly stoppered and allowed to stand at room temperature for 120 hours. After one day, yellow crystalline material had collected on the bottom of the flask. The reaction mixture was warmed gently on the steam bath for 15 minutes, cooled and poured into a water-ice mixture. The gum-like material that precipitated was extracted with several portions of chloroform. The chloroform solution was washed with aqueous potassium bicarbonate and with water and dried over sodium sulfate. Evaporation of the solvent left 7.5 g. of a light-colored solid. This material was triturated several times with boiling petroleum ether to remove unreacted keto ester. The residue was recrystallized from an ethyl acetate-petroleum ether mixture to give 6.5 g. (68%) of the desired compound, m.p. 153°–155°.

The nmr spectrum of this material was consistent with the assigned structure. From another preparation, the analytical sample, m.p. 150°–152°, was obtained after two recrystallizations from ethyl acetate-petroleum ether. It exhibited $\lambda_{max}^{EtOH}$ 310 m$\mu$ (log$\epsilon$ 3.996).

Anal. Calcd. for $C_{21}H_{28}OS_3$: C, 70.00; H, 7,78; S, 8.89; Found: C, 69.99; H, 7.99; S, 8.83

EXAMPLE 110

1,2-Dihydro-5,5-dimethyl-10-hydroxy-8-(3-methyl-2-octyl)-4H,5H-thiopyrano[3,4-d][1]benzopyran A Grignard reagent was prepared in a preflamed apparatus under an atmosphere of nitrogen by bubbling bromomethane into a 250 ml. 3-necked round bottom flask containing 2.03 g. (0.0833 mole) of magnesium in 50 ml. of dry ether. When the magnesium had all reacted, 10 ml. of ether was distilled from the reaction mixture to remove excess bromomethane. A solution of 3 g. (0.00733 mole) of the thiopyrone as prepared above was suspended in 30 ml. of dry benzene and 15 ml. of dry ether and was added dropwise to the Grignard solution during a period of 45 minutes. The reaction mixture was refluxed for five days, cooled and poured slowly into a mixture of 75 ml. of saturated ammonium chloride solution and 50 g. of ice. The benzene layer was separated and the aqueous layer was extracted several times with benzene. The combined extracts were washed with water, aqueous potassium bicarbonate solution, again with water, dried over sodium sulfate and then evaporated to give 3.5 g. of brown residue. This residue was dissolved in 150 ml. of dry n-heptane and when the solution was heated to boiling, four drops of 48% hydrobromic acid were added. After heating for 40 minutes, the solution was allowed to stand overnight and was filtered to remove a small amount of precipitate. Evaporation of the filtrate gave 2.6 g. (84%) of crude thiopyran. One gram of this material, purified in two 0.5 g. batches by heating in a sublimation apparatus at 150°/0.1 mm., gave 200 mg. of a yellow viscous oil of the desired compound.

The nmr spectrum of this oil was consistent with the structure of the desired product. Thin-layer chromatography (ethyl acetate/hexane, 1:9) showed a major spot ($R_f$ 0.80) and a minor spot ($R_f$ 0.74). The ultraviolet spectrum showed $\epsilon_{max}^{EtOH}$ 275 m$\mu$ (log$\epsilon$ 3.6).

Anal. Calcd. for $C_{23}H_{34}O_2S$: C, 73.74; H, 9.15; S, 8.56; Found: C, 73.57; H, 9.14; S, 8.76

EXAMPLE 111

1,2-Dihydro-5,5-dimethyl-8-(3-methyl-2-octyl)-10-[4-(piperidino)butyryloxy]-4H,5H-thiopyrano[3,4-c][1]benzopyran hydrochloride The benzopyran of Example 110 is reacted with $\gamma$-piperidinobutyric acid hydrochloride and dicyclohexylcarbodiimide according to the method of Example 98 to yield the desired ester.

EXAMPLE 112

Methyl 3-oxo-2,3,4,5-tetrahydro-6H-thiopyran-2-carboxylate

The procedure of Leonard and Figueras (J. Am. Chem. Soc. 74, 917 (1952)) was followed for the cyclization of 20 g. of carbmethoxymethyl $\gamma$-carbmethoxypropyl sulfide to give 11.1 g. (70%) of methyl 3-oxo-2,3,4,5-tetrahydro-6H-thiopyran-2-carboxylate. The structure was confirmed by Ir and nmr.

EXAMPLE 113

1,2-Dihydro-10-hydroxy-8-(3-methyl-2-octyl)-5-oxo-3H,5H-thiopyrano[2,3-c][1]benzopyran A solution of 14.2 g. (0.06 mole) of 5-(3-methyl-2-octyl)resorcinol and 11.1 g. (0.063 mole) of methyl-3-oxo2,3,4,5-tetrahydro-6H-thiopyran-2-carboxylate in 90 ml. of absolute ethanol was cooled in an ice-salt bath and saturated with anhydrous hydrogen chloride. After standing for 2 days at room temperature, the ethanol was removed on a rotary evaporator. The residue was dissolved in ether, washed with sodium bicarbonate solution and dried over sodium sulfate. Evaporation of the solvent gave 28.0 g. of residue which was chromatographed using Florisil (60-100 mesh) and graded methanol/chloroform solvent mixtures. A total of 10 g. of crude solid was obtained from the 1% methanol/chloroform fractions. The material was recrystallized twice from ethyl acetate/hexane to give 8.5 g. (40%) colorless crystals, m.p. 131°–133°. The proposed structure was confirmed by IR and nmr.

EXAMPLE 114

1,2-Dihydro-5,5-dimethyl-10-hydroxy-8-(3-methyl-2-octyl)-3H,5H-thiopyrano[2,3-c][1]benzopyran Methyl magnesium bromide was prepared by bubbling bromomethane into a mixture of 7.68 g. (0.32 mole) of magnesium turnings in ether. When all the magnesium had reacted, the solution was refluxed for a short time to remove the excess bromomethane. A solution of 6.96 g. (0.02 mole) of the pyrone (prepared as above) in benzene was added and the reaction mixture was kept at 45° for 24 hours. The reaction mixture was decomposed with saturated ammonium chloride; the organic layer was separated and the aqueous layer was extracted twice with ether. The organic layers were combined, washed with water, dried and evaporated to give a gummy residue. The IR and nmr spectra indicated the compound to be 5-(3-methyl-2-octyl)-2-[4,5-dihydro-2-(2-hydroxy-2-propyl)-6H-thiopyran-3-yl]resorcinol.

A small quantity of p-toluenesulfonic acid was added to a benzene solution of the above triol and the mixture was heated at reflux for 1½ hours in the presence of nitrogen. The benzene solution was washed with sodium bicarbonate solution, dried over sodium sulfate and evaporated to give a greenish-brown residue.

Chromatography using Florisil (60-100 mesh) and graded ether/pet ether solvent mixtures gave 5.2 g. (60%) of a nearly colorless gum. The gum exhibited $\lambda_{max}^{EtOH}$ 305 m$\mu$ (log $\epsilon$ 4.262) and the IR, nmr and UV spectra confirm the structure as 1,2-dihydro-5,5-dimethyl-10-hydroxy-8-(3-methyl-2-octyl)-3H,5H-thiopyrano-[2,3-c][1]benzopyran.

Anal. Calcd for $C_{23}H_{34}O_2S$: C, 73.73; H, 9.15; S, 8.54; Found: C, 73.55; H, 9.12; S, 8.45

EXAMPLE 115

1,2-Dihydro-5,5-dimethyl-8(3-methyl-2-octyl)-10-[4-(morpholino)butyryloxy]-3H,5H-thiopyrano[2,3-c][1]benzopyran hydrochloride The benzopyran of Example 114 is reacted with $\gamma$-morpholino butyric acid, hydrochloric salt and dicyclohexylcarbodiimide according to the method of Example 10 to yield the desired ester.

In the practice of this invention, improved anesthesia is obtained by pre-treating the subject to be anesthetized with from 1 to 5 mg./kg. of the compound useful in the practice of this invention, orally or intravenously from 0–120 minutes prior to the administration of the anesthetic agent, and preferably 15 minutes prior to the administration of the anesthetic. The compounds may be administered by either oral or parenteral routes, such as intravenously, intramuscularly and the like.

The presently preferred compounds useful in the practice of this invention are represented by the following formulae

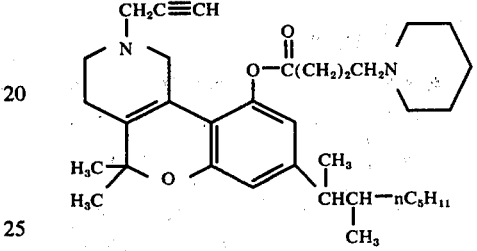

SP 106

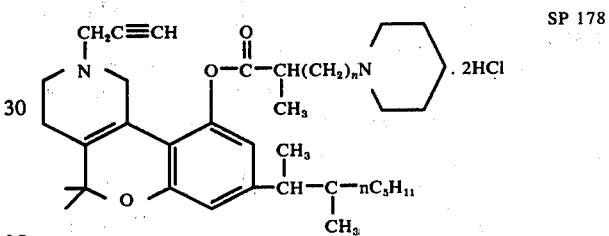

SP 178

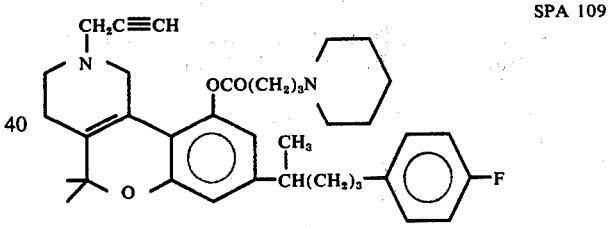

SPA 109

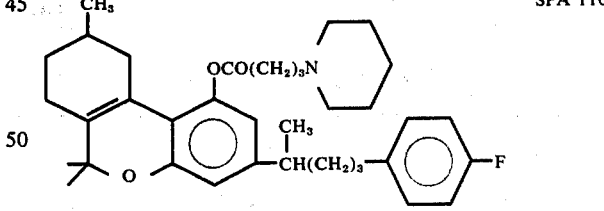

SPA 110

The following examples further illustrate this invention.

An intravenous potency/lethality ratio for Pentothal was established in mice as follows

EXAMPLE 116

Determination of the Anesthetic $ED_{50}$ and the $LD_{50}$ of Pentothal

Groups of 10 female Swiss-Webster (A. R. Schmidt, Madison, Wisconsin) mice weighing between 16–25 grams were used for all studies. Intravenous injections were made into the tail veins. The drugs were prepared daily in Sterile Water (Abbott List No. 1590). All animals were observed for one week following medication.

Onset and duration of anesthesia were noted with the loss of righting reflex being considered a positive test for anesthesia. $LD_{50}$'s $ED_{50}$'s, and their associated conficence limits were calculated by the method of Litchfield and Wilcoxon (1949).

The results are recorded in Table I.

TABLE I

| Drug: | Pentothal® |
|---|---|
| $LD_{50}$(95% C.L.) Mg./Kg.: | 76(72–79.7) |
| $ED_{50}$(95% C.L.) Mg./Kg.: | 20(16–24) |
| Therapeutic Index. | ~ 4 |
| Remarks: | Immediate onset, short duration, irritating (pH 11) |

EXAMPLE 117

Interaction of Benzopyranopyridines with Pentothal

RESULTS

1. Animals pretreated with SP-106, 1 mg./kg. intravenously 0-30 minutes prior to Pentothal, 10 mg./kg. (non-anesthetic dose) produced anesthesia (loss of righting reflex) with the peak effect at 5 minutes. Longer pretreatment times (60 to 120 minutes) had no effect.

2. Doses of 1 and 5 mg./kg. of SP-106 given intravenously 15 minutes prior to an anesthetic dose (30 mg./kg.) of Pentothal significantly lengthened the sleep.

EXAMPLE 118

Determination of Anesthetic Potency for Fluothane (halothane) and Penthrane

A modification of the method of Carson and Domino (*Anesthesiology*, 23:187–192, 1962) was used.

Groups of 10 female Swiss-Webster (A. R. Schmidt, Madison, Wisconsin) mice weighing between 16–24 grams were pre-treated with various doses or at various times with drug either oral or by intravenous injection of the tail veins. The mice were placed into 2 liter beakers (5 animals per beaker). The tops of the beakers were covered with Parafilm to which a gauze sponge had been attached. 0.1 cc of Penthrane or halothrane was injected through the Parafilm into the sponge at 5 minute intervals. The animals were observed for anesthesia (loss of righting reflex) and death (cessation of all movements). These parameters were measured by the use of a stop watch. Statistical analysis (one-way analysis of variance) was done on the computer

EXAMPLE 119

Interactions of Benzopyranopyridines with Fluothane (halothane) and Penthrane

1. Doses of 1 to 5 mg./kg. of SP-106 15 minutes prior to exposure of Penthrane vapors signficantly shortened onset to sleep, had no effect or lengthened time to death, and significantly lengthened the duration of anesthesia.

2. Doses of 1 to 5 mg./kg. of SP-106, 15 minutes prior to exposure to halothane vapors produced reduction of onset and increased the duration of anesthesia and time to death.

A number of benzopyran derivatives were screened in mice as adjuvants to the anesthetic actions of halothane. The Carson-Domino method (*Anesthesiology* 23:187, 1962) was used to measure anesthetic induction times and duration of anesthesia as evidenced by loss of righting reflex, as well as changes in the lethality of halothane.

Screening doses of 5 mg./kg. intravenously or 20 mg./kg. orally were used.

The findings are summarized in the following Table:

ACTIVITY OF BENZOPYRANS AS ADJUVANTS TO HALOTHANE ANESTHESIA:

| Treatment | | Dose | | Pretreat- | | | |
|---|---|---|---|---|---|---|---|
| SP-Number | Structure | mg/kg | Route | ment Time* | Onset | Duration | Lethality |
| SP-106 | 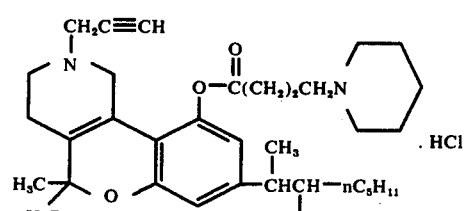 | 5 | i.v. | 15 | – | + | – |
| SP-178 | 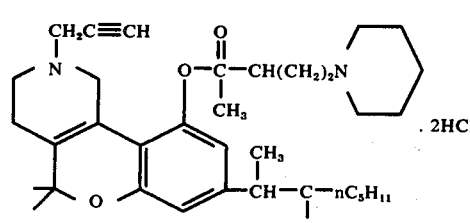 | 5 | i.v. | 15 | – | + | NE |

ACTIVITY OF BENZOPYRANS AS ADJUVANTS TO HALOTHANE ANESTHESIA: -continued

| Treatment SP-Number Structure | Dose mg/kg | Route | Pretreatment Time* | Onset | Duration | Lethality |
|---|---|---|---|---|---|---|
| SPA-109 | 5 | i.v. | 15 | – | + | NE |
| SP-102 | 5 | i.v. | 15 | + | + | NE |
| SP-117 | 5 | i.v. | 15 | + | (+) | NE |
| SP-190 | 5 | i.v. | 15 | – | + | NE |
| SP-112 | 5 | i.v. | 15 | – | + | NE |
| SP-159 | 5 | i.v. | 15 | – | + | NE |
| SP-1 | 20 | p.o. | 1 (hr) | + | + | – |
|  |  |  | 2 (hr) | – | + | NE |
|  |  |  | 3 (hr) | – | + | NE |
|  |  |  | 4 (hr) | – | + | NE |

-continued

ACTIVITY OF BENZOPYRANS AS ADJUVANTS TO HALOTHANE ANESTHESIA:

| Treatment SP-Number | Structure | Dose mg/kg | Route | Pretreatment Time* | Onset | Duration | Lethality |
|---|---|---|---|---|---|---|---|
| SP-111 | 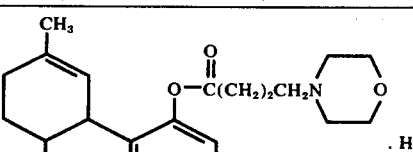 | 5 | i.v. | 15 (min) | — | + | NE |
| SP-204 | 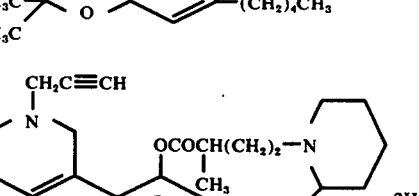 | 5 | i.v. | 15 | — | + | — |

\* = minutes (unless specified otherwise)
\+ = statistically significant increase
– = statistically significant decrease
NE = no effect
() = large but non-statistically significant change

We claim:
1. A method of pretreating a patient which is to be anesthetized with an anesthetic halothane, said method comprising administering to said patient from 0–120 minutes prior to the administration of said anesthetic halothane, a dose of from 1 to 5 mg./kg. body weight of a benzopyran of the formula

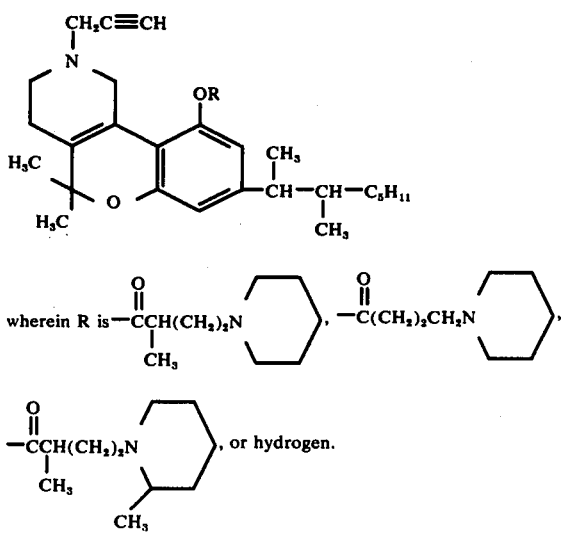

2. The method of claim 1 wherein the benzopyran is administered about 15 minutes prior to administration of the anesthetic.

3. The method of claim 1 wherein the benzopyran is 5,5-Dimethyl-10-[4-(1-piperidine)butyryloxy]-8-(3-methyl-2-octyl)-2-(2-propynyl)-1,2,3,4-tetrahydro-5H-[1]benzopyrano[3,4-d]pyridinehydrochloride.

4. The method of claim 1 wherein the benzopyran is 5,5-Dimethyl-10-hydroxy-8-(3-methyl-2-octyl)-2-(2-propynyl)-1, 2,3,4-tetrahydro-5H-[1]benzopyrano[3,4-d]pyridine-hydrochloride.

5. The method of claim 1 wherein the benzopyran is 5,5-Dimethyl-10-[4-(1-piperidine)α-methyl-butyryloxy]-8-(3-methyl-2-octyl)-2-(2-propynyl)-1,2,3,4-tetrahydro-5H-[1](benzopyrano[3,4-d]pyridine.

6. The method of claim 1 wherein the benzopyran is 5,5-Dimethyl-10-[4-(2-methyl-1-pipendine)α-methyl-butyryloxy]-8-(3-methyl-2-octyl)-2-(2-propynyl)-1,2,3,4-tetrahydro-5H-[1] benzopyrano[3,4-d]pyridine-hydrochloride.

7. The method of claim 1 wherein the anesthetic is administered by inhalation.

* * * * *